(12) United States Patent
Onichtchouk et al.

(10) Patent No.: US 8,501,473 B2
(45) Date of Patent: Aug. 6, 2013

(54) USE OF PLEITROPHIN FOR PREVENTING AND TREATING PANCREATIC DISEASES AND/OR OBESITY AND/OR METABOLIC SYNDROME

(75) Inventors: Daria Onichtchouk, Goettingen (DE); Ulrike Burk, Goettingen (DE)

(73) Assignee: Evotec International GmbH, Hamburg (DE)

( * ) Notice: Subject to any disclaimer, the term of this patent is extended or adjusted under 35 U.S.C. 154(b) by 1569 days.

(21) Appl. No.: 10/564,769

(22) PCT Filed: Jul. 15, 2004

(86) PCT No.: PCT/EP2004/007917
§ 371 (c)(1),
(2), (4) Date: Jun. 12, 2006

(87) PCT Pub. No.: WO2005/014022
PCT Pub. Date: Feb. 17, 2005

(65) Prior Publication Data
US 2010/0162421 A1    Jun. 24, 2010

(30) Foreign Application Priority Data
Jul. 16, 2003    (EP) .................................... 03016169

(51) Int. Cl.
*C12N 5/06* (2006.01)
*C12N 5/08* (2006.01)

(52) U.S. Cl.
USPC .......................................... 435/377; 435/325

(58) Field of Classification Search
None
See application file for complete search history.

(56) References Cited

U.S. PATENT DOCUMENTS

| 2002/0034768 A1 | 3/2002 | Shibuya et al. |
| 2003/0053989 A1 | 3/2003 | Kovesdi |
| 2003/0185794 A1 | 10/2003 | Colley |
| 2003/0202960 A1* | 10/2003 | Colley ......................... 424/85.1 |

FOREIGN PATENT DOCUMENTS

| WO | WO 9953943 | 10/1999 |
| WO | WO 0020869 | 4/2000 |
| WO | WO 0196394 | 12/2001 |
| WO | WO 0222176 | 3/2002 |

OTHER PUBLICATIONS

Deuel Thomas F et al: Pleiotrophin: A cytokine with diverse functions and a novel signaling pathway: Archives of Biochemistry and Biophysics, vol. 397, No. 2, Jan. 15, 2002, pp. 162-171, XP002304709.

Zhang N et al: Pleiotrophin and midkine, a family of mitogenic and angiogenic heparin-binding growth and differentiation factors: Current Opinion in Hematology, Rapid Science Publishers, Philadelphia, PA, US, vol. 6, No. 1, Jan. 1999, pp. 44-50, XP002122375.

* cited by examiner

*Primary Examiner* — Marianne P Allen
(74) *Attorney, Agent, or Firm* — Millen, White, Zelano, Branigan, P.C.

(57) ABSTRACT

The present invention discloses the protein pleiotrophin secreted by the developing pancreas, and polynucleotides, which identify and encode this protein. The invention also relates to the use of these sequences in the diagnosis, study, prevention, and treatment of pancreatic diseases (e.g. diabetes), obesity, and/or metabolic syndrome.

6 Claims, 7 Drawing Sheets

```
   1 ctctccctcc ctcgcccagc cttcgtcctc ctggcccgct cctctcatcc ctcccattct
  61 ccatttccct tccgttccct ccctgtcagg gcgtaattga gtcaaaggca ggatcaggtt
 121 ccccgccttc cagtccaaaa atcccgccaa gagagcccca gagcagagga aaatccaaag
 181 tggagagagg ggaagaaaga gaccagtgag tcatccgtcc agaaggcggg gagagcagca
 241 gcggcccaag caggagctgc agcgagccgg gtacctggac tcagcggtag caacctcgcc
 301 ccttgcaaca aaggcagact gagcgccaga gaggacgttt ccaactcaaa aatgcaggct
 361 caacagtacc agcagcagcg tcgaaaattt gcagctgcct tcttggcatt cattttcata
 421 ctggcagctg tggatactgc tgaagcaggg aagaaagaga accagaaaa aaaagtgaag
 481 aagtctgact gtggagaatg gcagtggagt gtgtgtgtgc ccaccagtgg agactgtggg
 541 ctgggcacac gggagggcac tcggactgga gctgagtgca agcaaaccat gaagacccag
 601 agatgtaaga tccctgcaa ctggaagaag caatttggcg cggagtgcaa ataccagttc
 661 caggcctggg gagaatgtga cctgaacaca gccctgaaga ccagaactgg aagtctgaag
 721 cgagccctgc acaatgccga atgccagaag actgtcacca tctccaagcc ctgtggcaaa
 781 ctgaccaagc ccaaacctca agcagaatct aagaagaaga aaaggaagg caagaaacag
 841 gagaagatgc tggattaaaa gatgtcacct gtggaacata aaaaggacat cagcaaacag
 901 gatcagttaa ctattgcatt tatatgtacc gtaggctttg tattcaaaaa ttatctatag
 961 ctaagtacac aataagcaaa aacaaaaaga aagaaaatt tttgtagtag cgttttttaa
1021 atgtatacta tagtaccagt aggggcttat aataaaggac tgtaatctta tttaggaagt
1081 tgacttatag tacatgataa atgatagaca attgaggtaa gttttttgaa attatgtgac
1141 attttacatt aaatttttt tacatttttt gggcagcaat ttaaatgtta tgactatgta
1201 aactacttct cttgttaggt aattttttc acctagattt ttttcccaat tgagaaaaat
1261 atatactaaa caaaaaaaaa aaaaaaaaaa aaaaaaaaa
```

Fig. 1A

```
   1 mqaqqyqqqr rkfaaaflaf ifilaavdta eagkkekpek kvkksdcgew qwsvcvptsg
  61 dcglgtregt rtgaeckqtm ktqrckipcn wkkqfgaeck yqfqawgecd lntalktrtg
 121 slkralhnae cqktvtiskp cgkltkpkpq aeskkkkkeg kkqekmld
```

Fig. 1B

SEQUENCE LISTING

```
<160> NUMBER OF SEQ ID NOS: 5

<210> SEQ ID NO 1
<211> LENGTH: 1300
<212> TYPE: DNA
<213> ORGANISM: human
<220> FEATURE:
<221> NAME/KEY: gene
<222> LOCATION: (1)..(1300)
<223> OTHER INFORMATION: nucleic acid sequence encoding the human DG001
      protein

<400> SEQUENCE: 1
ctctccctcc ctcgcccagc cttcgtcctc ctggcccgct cctctcatcc ctcccattct      60
ccatttccct tccgttccct ccctgtcagg gcgtaattga gtcaaaggca ggatcaggtt     120
ccccgccttc cagtccaaaa atcccgccaa gagagcccca gagcagagga aaatccaaag     180
tggagagagg ggaagaaaga gaccagtgag tcatccgtcc agaaggcggg gagagcagca     240
gcggcccaag caggagctgc agcgagccgg gtacctggac tcagcggtag caacctcgcc     300
ccttgcaaca aaggcagact gagcgccaga gaggacgttt ccaactcaaa aatgcaggct     360
caacagtacc agcagcagcg tcgaaaattt gcagctgcct tcttggcatt cattttcata     420
ctggcagctg tggatactgc tgaagcaggg aagaaagaga aaccagaaaa aaaagtgaag     480
aagtctgact gtgagaatg gcagtggagt gtgtgtgtgc ccaccagtgg agactgtggg     540
ctgggcacac gggagggcac tcggactgga gctgagtgca agcaaaccat gaagacccag     600
```

```
agatgtaaga tcccctgcaa ctggaagaag caatttggcg cggagtgcaa ataccagttc    660
caggcctggg gagaatgtga cctgaacaca gccctgaaga ccagaactgg aagtctgaag    720
cgagccctgc acaatgccga atgccagaag actgtcacca tctccaagcc ctgtggcaaa    780
ctgaccaagc ccaaacctca agcagaatct aagaagaaga aaaaggaagg caagaaacag    840
gagaagatgc tggattaaaa gatgtcacct gtggaacata aaaggacat cagcaaacag     900 gatcagttaa ctattgcatt tatatgtacc gtaggctttg tattcaaaaa ttatctatag    960
ctaagtacac aataagcaaa aacaaaaaga aagaaaatt tttgtagtag cgttttttaa    1020
atgtatacta tagtaccagt aggggcttat aataaaggac tgtaatctta tttaggaagt   1080
tgacttatag tacatgataa atgatagaca attgaggtaa gttttttgaa attatgtgac   1140
attttacatt aaatttttt tacatttttt gggcagcaat ttaaatgtta tgactatgta    1200
aactacttct cttgttaggt aattttttc acctagattt ttttcccaat tgagaaaaat    1260
atatactaaa caaaaaaaaa aaaaaaaaa aaaaaaaaa                            1300

<210> SEQ ID NO 2
<211> LENGTH: 168
<212> TYPE: PRT
<213> ORGANISM: human
<220> FEATURE:
<223> OTHER INFORMATION: amino acid sequence of human DG001 protein

<400> SEQUENCE: 2

Met Gln Ala Gln Gln Tyr Gln Gln Gln Arg Arg Lys Phe Ala Ala Ala
 1               5                  10                  15

Phe Leu Ala Phe Ile Phe Ile Leu Ala Ala Val Asp Thr Ala Glu Ala
            20                  25                  30

Gly Lys Lys Glu Lys Pro Glu Lys Val Lys Lys Ser Asp Cys Gly
        35                  40                  45

Glu Trp Gln Trp Ser Val Cys Val Pro Thr Ser Gly Asp Cys Gly Leu
    50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer 5'-3
<220> FEATURE:
<223> OTHER INFORMATION: mouse DG001 forward primer

<400> SEQUENCE: 3
```

```
caagtaccag ttccaggctt gg                                          22

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: primer 5'-3
<220> FEATURE:
<223> OTHER INFORMATION: mouse DG001 reverse primer

<400> SEQUENCE: 4
gctcgcttca ggctgcc                                                17

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: probe
<220> FEATURE:
<223> OTHER INFORMATION: mouse DG001 Taqman probe

<400> SEQUENCE: 5
tgacctcaat accgccttga agaccagaac                                  30
```

USE OF PLEITROPHIN FOR PREVENTING AND TREATING PANCREATIC DISEASES AND/OR OBESITY AND/OR METABOLIC SYNDROME

This invention relates to the use of low molecular weight DG001 proteins, to the use of polynucleotides encoding these, and to the use of effectors/modulators thereof in the diagnosis, study, prevention, and treatment of pancreatic diseases (e.g. diabetes mellitus), obesity and/or metabolic syndrome and to the use in regeneration of tissues such as pancreatic tissues and others.

Many human proteins serve as pharmaceutically active compounds. Several classes of human proteins that serve as such active compounds include hormones, cytokines, cell growth factors, and cell differentiation factors. Most proteins that can be used as a pharmaceutically active compound fall within the family of secreted proteins. Secreted proteins are generally produced within cells at rough endoplasmic reticulum, are then exported to the golgi complex, and then move to secretory vesicles or granules, where they are secreted to the exterior of the cell via exocytosis. Examples for commercially used secreted proteins are human insulin, thrombolytic agents, interferons, interleukins, colony stimulating factors, human growth hormone, transforming growth factor beta, tissue plasminogen activator, erythropoietin, and various other proteins. Receptors of secreted proteins, which are membrane-bound proteins, also have potential as therapeutic or diagnostic agents. It is, therefore, important for developing new pharmaceutical compounds to identify secreted proteins that can be tested for activity in a variety of animal models. Thus, in light of the pervasive role of secreted proteins in human physiology, a need exists for identifying and characterizing novel functions for human secreted proteins and the genes that encode them. This knowledge will allow one to detect, to treat, and to prevent medical diseases, disorders, and/or conditions by using secreted proteins or the genes that encode them.

The pancreas is an essential organ possessing both an exocrine function involved in the delivery of enzymes into the digestive tract and an endocrine function by which various hormones are secreted into the blood stream. The exocrine function is assured by acinar and centroacinar cells that produce various digestive enzymes and intercalated ducts that transport these enzymes in alkaline solution to the duodenum. The functional unit of the endocrine pancreas is the islet of Langerhans. Islets are scattered throughout the exocrine portion of the pancreas and are composed of four cell types: alpha-, beta-, delta- and PP-cells, reviewed for example in Kim S. K. and Hebrok M., (2001) Genes Dev. 15: 111-127. Beta-cells produce insulin, represent the majority of the endocrine cells and form the core of the islets, while alpha-cells secrete glucagon and are located in the periphery. Delta-cells and PP-cells are less numerous and secrete somatostatin and pancreatic polypeptide, respectively.

Early pancreatic development has been well studied in different species, including chicken, zebrafish, and mice (for an detailed review, see Kim & Hebrock, 2001, supra). The pancreas develops from distinct dorsal and ventral anlagen. Pancreas development requires specification of the pancreas structure along both anterior-posterior and dorsal-ventral axes. A number of transcription factors, which are critical for proper pancreatic development have been identified (see Kim & Hebrok, 2001, supra; Wilson M. E. et al. Mech Dev. 120: 65-80).

In postnatal/adult humans, the acinar and ductal cells retain a significant proliferative capacity that can ensure cell renewal and growth, whereas the islet cells become mostly mitotically inactive. This is in contrast to rodents where beta-cell replication is an important mechanism in the generation of new beta cells. It has been, suggested, that during embryonic development, pancreatic islets of Langerhans originate from differentiating duct cells or other cells with epithelial morphology (Bonner-Weir S. and Sharma A., (2002) J. Pathol. 197: 519-526; Gu G. et al., (2003) Mech Dev. 120: 35-43). In adult humans, new beta cells arise in the vicinity of ducts (Butler A. E. et al., (2003) Diabetes 52: 102-110; Bouwens L. and Pipeleers D. G., (1998) Diabetologia 41: 629-633). However, also an intra-islet location or an origin in the bone marrow has been suggested for precursor cells of adult beta cells (Zulewski H. et al., (2001) Diabetes 50: 521-533; Ianus A. et al., (2003) J Clin Invest. 111: 843-850). Pancreatic islet growth is dynamic and responds to changes in insulin demand, such as during pregnancy or during the increase in body mass occurring during childhood. In adults, there is a good correlation between body mass and islet mass (Yoon K. H. et al., (2003) J Clin Endocrinol Metab. 88: 2300-2308).

Pancreatic beta-cells secrete insulin, which is stimulated by high blood glucose levels. Insulin amongst other hormones plays a key role in the regulation of the fuel metabolism. Insulin leads to the storage of glycogen and triglycerides and to the synthesis of proteins. The entry of glucose into muscles and adipose cells is stimulated by insulin. In patients who suffer from diabetes mellitus the amount of insulin produced by the pancreatic islet cells is too low, resulting in elevated blood glucose levels (hyperglycemia). In diabetes type 1 beta cells are lost due to autoimmune destruction. In type 2 diabetic patients, liver and muscle cells loose their ability to respond to normal blood insulin levels (insulin resistance). High blood glucose levels (and also high blood lipid levels) lead to an impairment of beta-cell function and to an increase in beta-cell apoptosis. It is interesting to note that the rate of beta-cell neogenesis does not appear to change in type 2 diabetics (Butler et al., 2003, supra), thus causing a reduction in total beta-cell mass over time. Eventually the application of exogenous insulin becomes necessary in type 2 diabetics.

Improving metabolic parameters such as blood sugar and blood lipid levels (e.g. through dietary changes, exercise, medication or combinations thereof) before beta cell mass has fallen below a critical threshold leads to a relatively rapid restoration of beta cell function. However, after such a treatment the pancreatic endocrine function would remain impaired due to the only slightly increased regeneration rate.

In type 1 diabetics, the lifespan of pancreatic islets is dramatically shortened due to autoimmune destruction. Treatments have been devised which modulate the immune system and may be able to stop or strongly reduce islet destruction (Raz I. et al., (2001) Lancet 358: 1749-1753; Chatenoud L. et al., (2003) Nat Rev Immunol. 3: 123-132). However, due to the relatively slow regeneration of human beta cells such treatments could only be fully successful at improving the diabetic condition if they are combined with an agent which can stimulate beta cell regeneration. Thus, both for type 1 and type 2 diabetes (early and late stages) there is a need to find novel agents which stimulate beta cell regeneration.

Diabetes is a very disabling disease, because medications do not control blood sugar levels well enough to prevent swinging between high and low blood sugar levels. Patients with diabetes are at risk for major complications, including diabetic ketoacidosis, end-stage renal disease, diabetic retinopathy and amputation. There are also a host of related conditions, such as metabolic syndrome, obesity, hypertension, heart disease, peripheral vascular disease, and infections, for which persons with diabetes are at substantially increased risk. The treatment of these complications contributes to a considerable degree to the enormous cost which is imposed by diabetes on health care systems world wide.

Obesity is one of the most prevalent metabolic disorders in the world. It is still a poorly understood human disease that becomes as a major health problem more and more relevant for western society., Obesity is defined as a body weight more than 20% in excess of the ideal body weight, frequently resulting in a significant impairment of health. Obesity may be measured by body mass index, an indicator of adiposity or fatness. Further parameters for defining obesity are waist circumferences, skinfold thickness and bioimpedance. It is associated with an increased risk for cardiovascular disease, hypertension, diabetes mellitus type II, hyperlipidaemia and an increased mortality rate. Obesity is influenced by genetic, metabolic, biochemical, psychological, and behavioral factors and can be caused by different reasons such as non-insulin dependent diabetes, increase in triglycerides, increase in carbohydrate bound energy and low energy expenditure (Kopelman P. G., (2000) Nature 404: 635-643).

The concept of 'metabolic syndrome' (syndrome x, insulin-resistance syndrome, deadly quartet) was first described 1966 by Camus and reintroduced 1988 by Reaven (Camus JP, 1966, Rev Rhum Mal Osteoartic 33: 10-14; Reaven et al. 1988, Diabetes, 37: 1595-1607). Today, metabolic syndrome is commonly defined as clustering of cardiovascular risk factors like hypertension, abdominal obesity, high blood levels of triglycerides and fasting glucose as well as low blood levels of HDL cholesterol. Insulin resistance greatly increases the risk of developing the metabolic syndrome (Reaven, 2002, Circulation 106: 286-288). The metabolic syndrome often precedes the development of type II diabetes and cardiovascular disease (Lakka H. M., 2002, JAMA 288: 2709-2716). The control of blood lipid levels and blood glucose levels is essential for the treatment of the metabolic syndrome (see, for example, Santomauro A. T. et al., (1999) Diabetes, 48: 1836-1841).

The molecular factors regulating food intake and body weight balance are incompletely understood. Even if several candidate genes have been described which are supposed to influence the homeostatic system(s) that regulate body mass/weight, like leptin or the peroxisome proliferator-activated receptor-gamma co-activator, the distinct molecular mechanisms and/or molecules influencing obesity or body weight/body mass regulations are not known.

There is a need in the prior art for the identification of candidate genes that are specifically expressed in early development in certain pancreatic tissues. These genes and the thereby encoded proteins can provide tools to the diagnosis and treatment of severe pancreatic disorders and related diseases. Therefore, this invention describes secreted proteins that are specifically expressed in pancreatic tissues early in the development. The invention relates to the use of these genes and proteins in the diagnosis, prevention and/or treatment of pancreatic dysfunctions, such as diabetes, and other related diseases such as obesity and/or metabolic syndrome. These proteins and genes are especially useful in regeneration processes, such as regeneration of the pancreas cells.

In this invention, we disclose a secreted factor referred to as DG001 which is involved in pancreas development, regeneration, and in the regulation of energy homeostasis. DG001 corresponds to human pleiotrophin, a member of the cytokine/growth factor family of proteins, which is a secreted heparin-binding cytokine that signals diverse functions involved with angiogenesis, neuorogenesis, cell migration, and mesoderm-epithelial interactions (for reviews, see, Deuel T. F. et al., (2002) Arch Biochem Biophys. 397: 162-171; Zhang N. and Deuel T. F, (1999) Curr Opin Hematol. 6: 44-50). Pleiotrophin is developmentally regulated and highly conserved among species.

Pleiotrophin gene expression is found in cells in early differentiation during different development periods and is upregulated in cells with an early differentiation phenotype in wound repair. Pleiotrophin expression also increases upon ischemic injury.

In the non-cancerous state, pleiotrophin is very tightly regulated, being expressed only in regions of the brain and reproductive tract. Widespread deregulation of pleiotrophin is found in many known human cancers or their derived cell lines. In different human tumor cells, the pleiotrophin gene is strongly expressed. Expression of the pleiotrophin gene in tumor cells in vivo accelerates growth and stimulates tumor angiogenesis. In addition to this regulation of tumor cells, pleiotrophin is causing differential growth of osteoblasts and cranial nerve cells.

Pleiotrophin is the first ligand of any of the known transmembrane tyrosine phosphatases. A chondroitin sulfate proteoglycan (protein-tyrosine phosphatase zeta, PTPzeta) was identified as a receptor for pleiotrophin which is inactivated by pleiotrophin. Pleiotrophin thus regulates both normal cell functions and different pathological conditions at many levels. It signals these functions through a transmembrane tyrosine phosphatase.

Accordingly, certain uses of DG001 have been described in several patent applications. For example, DG001 was suggested to be used to inhibit cellular growth and control angiogenesis, useful for controlling post-surgical bleeding (EP535337-A2), cancer (EP535337-A2), such as prostate cancer (WO 00/055174), or brain tumors (WO 02/76510), for treatment and diagnosis of osteoporosis (WO 92/00324), for nerve repair and for treating neurodegenerative disorders (EP474979-A; WO 99/53943; dementia (WO 92/00324), cardiac (coronary artery disease, ischaemic heart disease), kidney and inflammatory disorders (WO 99/53943, WO 00/35473), diabetic peripheral vasculopathies and peripheral atherosclerotic disease (WO 99/53943), or to inhibit the infectivity of Herpesviridae virus (EP569703-A2).

Accordingly, the present invention relates to a secreted protein with novel functions in the human metabolism, regeneration, and pancreatic developmental processes. The present invention discloses specific genes and proteins encoded thereby and effectors/modulators thereof involved in the regulation of pancreatic function and metabolism, especially in pancreas diseases such as diabetes mellitus, e.g. insulin dependent diabetes mellitus and/or non-insulin dependent diabetes mellitus, and/or metabolic syndrome, obesity, and/or related disorders such as coronary heart disease, eating disorder, cachexia, hypertension, hypercholesterolemia (dyslipidemia), liver fibrosis, and/or gallstones. Further, the present invention relates to specific genes and proteins encoded thereby and effectors/modulators thereof involved in the modulation, e.g. stimulation, of pancreatic development and/or the regeneration of pancreatic cells or tissues, e.g. cells having exocrinous functions such as acinar cells, centroacinar cells and/or ductal cells, and/or cells having endocrinous functions, particularly cells in Langerhans islets such as alpha-, beta-, delta- and/or PP-cells, more particularly beta-cells.

In this invention, we used a screen for secreted factors expressed in developing mammalian (mouse) pancreas, as described in more detail in the Examples section (see Example 1). This screen identified DG001 as secreted factor expressed in developing mouse pancreas. The present invention describes mammalian DG001 proteins and the polynucleotides encoding these, in particular human DG001, as being involved in the conditions and processes mentioned above.

The present invention relates to DG001 polynucleotides encoding polypeptides with novel functions in the development and regeneration of pancreatic tissues and thus in mammalian pancreatic diseases (e.g. diabetes), and also in body-weight regulation, energy homeostasis, and obesity, fragments of said polynucleotides, polypeptides encoded by said polynucleotides or fragments thereof. The invention also relates to vectors, host cells and recombinant methods for producing the polypeptides and polynucleotides of the invention. The invention also relates to effectors/modulators of DG001 polynucleotides and/or polypeptides, e.g. antibodies, biologically active nucleic acids, such as antisense molecules, RNAi molecules or ribozymes, aptamers, peptides or low-molecular weight organic compounds recognizing said polynucleotides or polypeptides.

DG001 homologous proteins and nucleic acid molecules coding therefore are obtainable from vertebrate species. Particularly preferred are nucleic acids encoding the human DG001 protein and variants thereof. The invention particularly relates to a nucleic acid molecule encoding a polypeptide contributing to regulating the energy homeostasis and the mammalian metabolism, wherein said nucleic acid molecule comprises
(a) the nucleotide sequence of human DG001 (SEQ ID NO: 1) and/or a sequence complementary thereto,
(b) a nucleotide sequence which hybridizes at 50° C. in a solution containing 1×SSC and 0.1% SDS to a sequence of (a),
(c) a sequence corresponding to the sequences of (a) or (b) within the degeneration of the genetic code,
(d) a sequence which encodes a polypeptide which is at least 85%, preferably at least 90%, more preferably at least 95%, more preferably at least 98% and up to 99.6% identical to the amino acid sequences of the human DG001 protein (SEQ ID NO: 2),
(e) a sequence which differs from the nucleic acid molecule of (a) to (d) by mutation and wherein said mutation causes an alteration, deletion, duplication and/or premature stop in the encoded polypeptide or
(f) a partial sequence of any of the nucleotide sequences of (a) to (e) having a length of 15-25 bases, preferably 25-35 bases, more preferably 35-50 bases and most preferably at least 50 bases.

The function of the mammalian DG001 in mammalian metabolism was validated by analyzing the expression of the transcripts in different tissues and by analyzing the role in adipocyte differentiation (see Example 3 and FIG. 2 for more detail). In mouse models of insulin resistance and/or diabetes expression, DG001 is strongly down-regulated in metabolic active tissue (WAT) which is supporting an essential role of DG001 in the regulation of the mammalian metabolism, particularly in processes related to, obesity, diabetes, or metabolic syndrome (FIG. 2B). In addition, expression of DG001 mRNA is significantly down-regulated in WAT in mice showing symptoms of diabetes, lipid accumulation, and high plasma lipid levels, if fed a high fat diet. Further, the expression of DG001 is up-regulated in BAT and muscle tissues in these mice (FIG. 2C). Thus, DG001 protein is playing a role in the regulation of metabolism, particularly energy homeostasis and thermogenesis.

Further, we show (see Examples) that the DG001 protein has to be down-regulated at a very early stage of adipose differentiation (until day 4) and upregulated during the late stage in order for the preadipocyctes to differentiate into mature adipocytes. With regard to changes in expression intensity during the differentiation of preadipocytes to adipocytes, a slight reduction in relative signal intensity can be observed for DG001 during the in vitro differentiation program of 3T3-L1 (see FIG. 2D). The results are suggesting a role of DG001 as modulator of adipogenesis.

Microarrays are analytical tools routinely used in bioanalysis. A microarray has molecules distributed over, and stably associated with, the surface of a solid support. The term "microarray" refers to an arrangement of a plurality of polynucleotides, polypeptides, antibodies, or other chemical compounds on a substrate. Microarrays of polypeptides, polynucleotides, and/or antibodies have been developed and find use in a variety of applications, such as monitoring gene expression, drug discovery, gene sequencing, gene mapping, bacterial identification, and combinatorial chemistry. One area in particular in which microarrays find use is in gene expression analysis (see Example 4). Array technology can be used to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for identifying genes that are tissue specific, are affected by a substance being tested in a toxicology assay, are part of a signaling cascade, carry out housekeeping functions, or are specifically related to a particular genetic predisposition, condition, disease, or disorder.

Microarrays may be prepared, used, and analyzed using methods known in the art (see for example, Brennan, T. M. et al. (1995) U.S. Pat. No. 5,474,796; Schena, M. et al. (1996) Proc. Natl. Acad. Sci. 93: 10614-10619; Baldeschweiler et al., PCT application WO 95/251116; Shalon, D. et al., PCT application WO 95/35505; Heller, R. A. et al. (1997) Proc. Natl. Acad. Sci. 94: 2150-2155; Heller, M. J. et al. (1997) U.S. Pat. No. 5,605,662). Various types of microarrays are well known and thoroughly described in Schena, M., ed. (1999; DNA Microarrays: A Practical Approach, Oxford University Press, London).

Oligonucleotides or longer fragments derived from any of the polynucleotides described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

As determined by microarray analysis, DG001 shows differential expression in 3T3-L1 cells. A strong up-regulation is observed concerning the expression of DG001 during adipocyte differentiation (see FIG. 2E). The DG001 protein in preadipocyctes has the potential to enhance adipose differentiation at a very early stage. Therefore, the DG001 protein might play an essential role in adipogenesis. The results are suggesting a role of DG001 in the regulation in human metabolism, for example, as effector/modulator (for example, enhancer) of adipogenesis. Thus, DG001 is a strong candidate for the manufacture of a pharmaceutical composition and a medicament for the treatment of conditions related to human metabolism, such as diabetes, obesity, and/or metabolic syndrome.

This invention further shows that DG001 induces the differentiation of insulin-producing cells and is thus a target for the treatment of diabetes. In connection with the present invention, the term "progenitor cells" relates to undifferentiated cells capable of being differentiated into insulin producing cells. The term particularly includes stem cells, i.e. undifferentiated or immature embryonic, adult, or somatic cells that can give rise to various specialized cell types. The term "stem cells" can include embryonic stem cells (ES) and primordial germ cells (EG) cells of mammalian, e.g. human or animal origin. Isolation and culture of such cells is well known to those skilled in the art (see, for example, Thomson et al., (1998) Science 282: 1145-1147; Shamblott et al., (1998) Proc. Natl. Acad. Sci. USA 95: 13726-13731; U.S. Pat. No. 6,090,622; U.S. Pat. No. 5,914,268; WO 00/27995; Notarianni et al., (1990) J. Reprod. Fert. 41: 51-56; Vassilieva et al., (2000) Exp. Cell. Res. 258: 361-373). Adult or somatic stem cells have been identified in numerous different tissues such as intestine, muscle, bone marrow, liver, and brain. WO 03/023018 describes a novel method for isolating, culturing, and differentiating intestinal stem cells for therapeutic use. In the pancreas, several indications suggest that stem cells are also present within the adult tissue (Gu and Sarvetnick, (1993) Development 118: 33-46; Bouwens, (1998) Microsc Res Tech 43: 332-336; Bonner-Weir, (2000) J. Mol. Endocr. 24: 297-302).

Embryonic stem cells can be isolated from the inner cell mass of pre-implantation embryos (ES cells) or from the primordial germ cells found in the genital ridges of post-implanted embryos (EG cells). When grown in special culture conditions such as spinner culture or hanging drops, both ES and EG cells aggregate to form embryoid bodies (EB). EBs are composed of various cell types similar to those present during embryogenesis. When cultured in appropriate media, EB can be used to generate in vitro differentiated phenotypes, such as extraembryonic endoderm, hematopoietic cells, neurons, cardiomyocytes, skeletal muscle cells, and vascular cells. We have previously described a method that allows EB to efficiently differentiate into insulin-producing cells (as described in patent application PCT/EP02/04362, published as WO 02/086107 and by Blyszczuk et al., (2003) Proc. Natl. Acad Sci USA 100: 998-1003, which are incorporated herein by reference).

The results shown in FIG. 3 clearly demonstrate an induction of the differentiation of insulin-producing cells by DG001. Thus, DG001 can induce the differentiation of beta-cells and is therefore a target for therapeutic uses in the treatment of diabetes, for example, when regeneration of cells is required.

Before the present invention is described, it is understood that all technical and scientific terms used herein have the same meanings as commonly understood by one of ordinary skill in the art to which this invention belongs.

In the present invention the term "beta-cell regeneration" refers to an at least partial restoration of normal beta-cell function by increasing the number of functional insulin secreting beta-cells and/or by restoring normal function in functionally impaired beta-cells.

The invention also encompasses polynucleotides that encode the proteins of the invention and homologous proteins. Accordingly, any nucleic acid sequence, which encodes the amino acid sequences of the proteins of the invention and homologous proteins, can be used to generate recombinant molecules that express the proteins of the invention and homologous proteins. In a particular embodiment, the invention encompasses a nucleic acid encoding DG001. It will be appreciated by those skilled in the art that as a result of the degeneracy of the genetic code, a multitude of nucleotide sequences encoding the proteins, some bearing minimal homology to the nucleotide sequences of any known and naturally occurring gene, may be produced. The invention contemplates each and every possible variation of nucleotide sequence that can be made by selecting combinations based on possible codon choices.

Also encompassed by the invention are polynucleotide sequences that are capable of hybridizing to the claimed nucleotide sequences, and in particular, those of the polynucleotide encoding the proteins of the invention, under various conditions of stringency. Hybridization conditions are based on the melting temperature (Tm) of the nucleic acid binding complex or probe, as described in Wahl & Berger (1987: Methods Enzymol. 152: 399-407) and Kimmel (1987; Methods Enzymol. 152: 507-511), and may be used at a defined stringency. Preferably, hybridization under stringent conditions means that after washing for 1 h with 1×SSC and 0.1% SDS at 50° C., preferably at 55° C., more preferably at 62° C. and most preferably at 65° C., particularly for 1 h in 0.2×SSC and 0.1% SDS at 50° C., preferably at 55° C., more preferably at 62° C. and most preferably at 65° C., a positive hybridization signal is observed. Altered nucleic acid sequences encoding the proteins which are encompassed by the invention include deletions, insertions or substitutions of different nucleotides resulting in a polynucleotide that encodes the same or a functionally equivalent protein.

The encoded proteins may also contain deletions, insertions or substitutions of amino acid residues, which produce a silent change and result in functionally equivalent proteins. Deliberate amino acid substitutions may be made on the basis of similarity in polarity, charge, solubility, hydrophobicity, hydrophilicity, and/or the amphipathic nature of the residues as long as the biological activity of the protein is retained. Furthermore, the invention relates to peptide fragments of the proteins or derivatives thereof such as cyclic peptides, retro-inverso peptides or peptide mimetics having a length of at least 4, preferably at least 6 and up to 50 amino acids.

Also included within the scope of the present invention are alleles of the genes encoding the proteins of the invention and homologous proteins. As used herein, an 'allele' or 'allelic sequence' is an alternative form of the gene, which may result from at least one mutation in the nucleic acid sequence. Alleles may result in altered mRNAs or polypeptides whose structures or function may or may not be altered. Any given gene may have none, one or many allelic forms. Common mutational changes, which give rise to alleles, are generally ascribed to natural deletions, additions or substitutions of nucleotides. Each of these types of changes may occur alone or in combination with the others, one or more times in a given sequence.

The nucleic acid sequences encoding DG001 and homologous proteins may be extended utilizing a partial nucleotide sequence and employing various methods known in the art to detect upstream sequences such as promoters and regulatory elements.

In order to express a biologically active protein, the nucleotide sequences encoding the proteins or functional equivalents, may be inserted into appropriate expression vectors, i.e., a vector which contains the necessary elements for the transcription and translation of the inserted coding sequence.

Methods, which are well known to those skilled in the art, may be used to construct expression vectors containing sequences encoding the proteins and the appropriate transcriptional and translational control elements. Regulatory elements include for example a promoter, an initiation codon, a stop codon, a mRNA stability regulatory element, and a polyadenylation signal. Expression of a polynucleotide can be assured by (i) constitutive promoters such as the Cytomegalovirus (CMV) promoter/enhancer region, (ii) tissue specific promoters such as the insulin promoter (see, Soria et al., 2000, Diabetes 49: 157), SOX2 gene promoter (see Li et al., (1998) Curr. Biol. 8: 971-974), Msi-1 promoter (see Sakakibara et al., (1997) J. Neuroscience 17: 8300-8312), alpha-cardia myosin heavy chain promoter or human atrial natriuretic factor promoter (Klug et al., (1996) J. Clin. Invest 98: 216-224; Wu et al., (1989) J. Biol. Chem. 264: 6472-6479) or (iii) inducible promoters such as the tetracycline inducible system. Expression vectors can also contain a selection agent or marker gene that confers antibiotic resistance such as the neomycin, hygromycin or puromycin resistance genes. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y. and Ausubel, F. M. et al. (1989) Current Protocols in Molecular Biology, John Wiley & Sons, New York, N.Y.

In a further embodiment of the invention, natural, modified or recombinant nucleic acid sequences encoding the proteins of the invention and homologous proteins may be ligated to a heterologous sequence to encode a fusion protein.

A variety of expression vector/host systems, as known in the art, may be utilized to contain and express sequences encoding the proteins or fusion proteins. These include, but are not limited to, micro-organisms such as bacteria transformed with recombinant bacteriophage, plasmid or cosmid DNA expression vectors; yeast transformed with yeast expression vectors; insect cell systems infected with virus expression vectors (e.g., baculovirus, adenovirus, adeno-associated virus, lentiverus, retrovirus); plant cell systems transformed with virus expression vectors (e.g., cauliflower mosaic virus, CaMV; tobacco mosaic virus, TMV) or with bacterial expression vectors (e.g., Ti or PBR322 plasmids); or animal cell systems.

The presence of polynucleotide sequences of the invention in a sample can be detected by DNA-DNA or DNA-RNA hybridization and/or amplification using probes or portions or fragments of said polynucleotides. Nucleic acid amplification based assays involve the use of oligonucleotides or oligomers based on the sequences specific for the gene to detect transformants containing DNA or RNA encoding the corresponding protein. As used herein 'oligonucleotides' or 'oligomers' refer to a nucleic acid sequence of at least about 10 nucleotides and as many as about 60 nucleotides, preferably about 15 to 30 nucleotides, and more preferably about 20-25 nucleotides, which can be used as a probe or amplimer.

A wide variety of labels and conjugation techniques are known by those skilled in the art and may be used in various nucleic acid and amino acid assays. Means for producing labeled hybridization or PCR probes for detecting polynucleotide sequences include oligo-labeling, nick translation, end-labeling of RNA probes, PCR amplification using a labeled nucleotide, or enzymatic synthesis. These procedures may be conducted using a variety of commercially available kits (Pharmacia & Upjohn, (Kalamazoo, Mich.); Promega (Madison Wis.); and U.S. Biochemical Corp., (Cleveland, Ohio).

The presence of DG001 in a sample can be determined by immunological methods or activity measurement. A variety of protocols for detecting and measuring the expression of proteins, using either polyclonal or monoclonal antibodies specific for the protein or reagents for determining protein activity are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the protein is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158: 1211-1226).

Suitable reporter molecules or labels, which may be used, include radionuclides, enzymes, fluorescent, chemiluminescent or chromogenic agents as well as substrates, co-factors, inhibitors, magnetic particles, and the like.

Host cells transformed with nucleotide sequences encoding a protein of the invention may be cultured under conditions suitable for the expression and recovery of said protein from cell culture. The protein produced by a recombinant cell may be secreted or contained intracellularly depending on the sequence or/and the vector used. As will be understood by those of skill in the art, expression vectors containing polynucleotides, which encode the protein may be designed to contain signal sequences, which direct secretion of the protein through a prokaryotic or eukaryotic cell membrane. Other recombinant constructions may be used to join sequences encoding the protein to nucleotide sequence encoding a polypeptide domain, which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.) The inclusion of cleavable linker sequences such as those specific for Factor XA or Enterokinase (Invitrogen, San Diego, Calif.) between the purification domain and the desired protein may be used to facilitate purification.

The data disclosed in this invention show that the DG001 nucleic acids and proteins and effector/modulator molecules thereof are useful in diagnostic and therapeutic applications implicated, for example, but not limited to, pancreatic diseases (such as diabetes mellitus, e.g. insulin dependent diabetes mellitus and/or non-insulin dependent diabetes mellitus), obesity, metabolic syndrome, eating disorder, cachexia, hypertension, coronary heart disease, hypercholesterolemia (dyslipidemia), and/or gallstones. Further, the data show that the DG001 nucleic acids and proteins and effector/modulator molecules thereof are useful for the modulation, e.g. stimulation, of pancreatic development and/or the regeneration of pancreatic cells or tissues, e.g. cell having exocrinous functions such as acinar cells, centroacinar cells and/or ductal cells, and/or cells having endocrinous functions, particularly cells in Langerhans islets such as alpha-, beta-, delta- and/or PP-cells, more particularly beta-cells. Hence, diagnostic and therapeutic uses for the proteins of the invention nucleic acids and proteins of the invention are, for example but not limited to, the following: (i) tissue regeneration in vitro and in vivo (regeneration for all these tissues and cell types composing these tissues and cell types derived from these tissues), (ii) small molecule drug target, (iii) antibody target (therapeutic, diagnostic, drug targeting/cytotoxic antibody), (iv) diagnostic and/or prognostic marker, (v) protein therapy, (vi) gene therapy (gene delivery/gene ablation), and/or (vii) research tools.

According to this invention the DG001 product may be administered
i) as a pharmaceutical composition e.g. enterally, parenterally or topically, preferably directly to the pancreas,
ii) via implantation of DG001 protein product expressing cells, and/or
iii) via gene therapy
as described in more detail below.

Further, the DG001 expression level in a patient may be influenced by a DG001 modulator/effector administered
i) as a pharmaceutical composition e.g. enterally, parenterally or topically, preferably directly to the pancreas,
ii) via cell based therapy, and/or
iii) via gene therapy
as described in more detail below.

The DG001 product or the DG001 modulator/effector, i.e. a pharmaceutically active substance influencing, particularly increasing the DG001 expression level or function may be administered in the above described manner alone or in combination with another pharmaceutical composition useful to treat beta-cell degeneration, for example hormones, growth factors or immune modulating agents.

A DG001 product or a modulator/effector thereof may be administered in patients suffering from a disease going along with impaired beta-cell function, for example but not limited to diabetes type 1, LADA, or progressed diabetes type 2. It is further contemplated that a DG001 product or the modulator/effector thereof may be administered preventively to patients at risk to develop beta-cell degeneration, like for example but not limited to patients suffering from diabetes type 2 or LADA in early stages. A variety of pharmaceutical formulations and different delivery techniques are described in further detail below.

The present invention also relates to methods for differentiating progenitor cells into insulin-producing cells in vitro comprising
(a) activating one or more pancreatic genes in a progenitor, e.g. stem cell (optional step, particularly if embryonic stem cells are used)
(b) aggregating said cells to form embryoid bodies (optional step, particularly if embryonic stem cells are used)
(c) cultivating embryoid bodies or cultivating adult stem cells (e.g., duct cells) in specific differentiation media containing a DG001 protein product and/or a modulator/effector thereof under conditions wherein beta-cell differentiation is significantly enhanced, and
(d) identifying and selecting insulin-producing cells.

Activation of pancreatic genes may comprise transfection of a cell with pancreatic gene operatively linked to an expression control sequence, e.g. on a suitable transfection vector, as described in WO 03/023018, which is herein incorporated by reference. Examples of preferred pancreatic genes are Pdx1, Pax4, Pax6, neurogenin 3 (ngn3), Nkx 6.1, Nkx 6.2, Nkx 2.2, HB 9, BETA2/Neuro D, Isl 1, HNF1-alpha, HNF1-beta and HNF3 of human or animal origin. Each gene can be used individually or in combination with at least one other gene. Pax4 is especially preferred.

DG001 products, e.g. DG001 protein or nucleic acid products, are preferably produced via recombinant techniques because such methods are capable of achieving high amounts of protein at a great purity, but are not limited to products expressed in bacterial, plant, mammalian, or insect cell systems.

Further, the data show that the DG001 nucleic acids and proteins and effector/modulator molecules thereof are useful for the modulation, e.g. stimulation, of pancreatic development and/or for the regeneration of pancreatic cells or tissues, e.g. cells having exocrinous functions such as acinar cells, centroacinar cells and/or ductal cells, and/or cells having endocrinous functions, particularly cells in Langerhans islets such as alpha-, beta-, delta- and/or PP-cells, more particularly beta-cells.

For example, but not limited to, cDNAs encoding the proteins of the invention and particularly their human homologues may be useful in stimulating, enhancing or regulating the regeneration of tissues, and the proteins of the invention and particularly their human homologues may be useful when administered to a subject in need thereof. By way of non-limiting example, the compositions of the present invention will have efficacy for treatment of patients suffering from, for example, pancreatic diseases (e.g. diabetes), obesity, and/or metabolic syndrome as described above.

Beside diabetes, the compositions of the present invention will also have efficacy for treatment of patients with other pancreatic diseases such as pancreatic cancer, dysplasia, or pancreatitis.

The DG001 nucleic acids and proteins and effectors/modulators thereof are useful in diagnostic and therapeutic applications implicated in various embodiments as described below. For example, but not limited to, cDNAs encoding the proteins of the invention and particularly their human homologues may be useful in gene therapy, and the proteins of the invention and particularly their human homologues may be useful when administered to a subject in need thereof. By way of non-limiting example, the compositions of the present invention will have efficacy for treatment of patients suffering from, for example, pancreatic diseases (e.g. diabetes), obesity, and/or metabolic syndrome as described above.

DG001 product cell therapy, i.e. pancreatic implantation of cells producing DG001 protein product, is also contemplated. This embodiment involves implanting cells capable of synthesizing and secreting a biologically active form of DG001 protein product into patients. Such DG001 protein product-producing cells may be cells that are natural producers of DG001 protein product or may be cells that are modified to express the protein. Such modified cells include recombinant cells whose ability to produce a DG001 protein product has been augmented by transformation with a gene encoding the desired DG001 protein product in a vector suitable for promoting its expression and secretion. In order to minimize a potential immunological reaction in patients being administered DG001 protein product of a foreign species, it is preferred that the cells producing DG001 protein product be of human origin and produce human DG001 protein product. Likewise, it is preferred that the recombinant cells producing DG001 protein product be transformed with an expression vector containing a gene encoding a human DG001 protein product. Implanted cells may be encapsulated to avoid infiltration of surrounding tissue. Human or nonhuman animal cells may be implanted in patients in biocompatible, semipermeable polymeric enclosures or membranes that allow release of DG001 protein product, but that prevent destruction of the cells by the patient's immune system or by other detrimental factors from the surrounding tissue.

Alternatively, DG001 protein product secreting cells may be introduced into a patient in need intraportally via a percutaneous transhepatic approach using local anaesthesia. Between 3000 and 100 000 equivalent differentiated insulin-producing cells per kilogram body weight are preferably administered. Such surgical techniques are well known in the art and can be applied without any undue experimentation, see Pyzdrowski et al, 1992, New England J. Medicine 327: 220-226; Hering et al., Transplantation Proc. 26:570-571, 1993; Shapiro et al., New England J. Medicine 343:230-238, 2000.

In a further preferred embodiment, DG001 protein product can be delivered directly to progenitor, e.g. stem cells in order to stimulate the differentiation of insulin producing cells. For example, protein delivery can be achieved by polycationic liposomes (Sells et al. (1995) Biotechniques 19:72-76), Tat-mediated protein transduction (Fawell et al. (1993) Proc. Natl. Acad. Sci. USA 91:664-668) and by fusing a protein to the cell permeable motif derived from the PreS2-domain of the hepatitis-B virus (Oess and Hildt (2000) Gene Ther. 7:750-758). Preparation, production and purification of such proteins from bacteria, yeast or eukaryotic cells are well known by persons skilled in the art. In this embodiment of the invention, DG001 may be added preferably at concentrations between 1 ng/ml and 500 ng/ml, more preferably between 10 and 100 ng/ml, e.g. at about 50 ng/ml.

Further, the invention relates to a cell preparation comprising differentiated progenitor cells, e.g. stem cells exhibiting insulin production, particularly an insulin-producing cell line obtainable by the method described above. The insulin-producing cells may exhibit a stable or a transient expression of at least one pancreatic gene involved in beta-cell differentiation. The cells are preferably human cells that are derived from human stem cells. For therapeutic applications the production of autologous human cells from adult stem cells of a patient is especially preferred. However, the insulin producing cells may also be derived from non-autologous cells. If necessary, undesired immune reactions may be avoided by encapsulation, immunosuppression and/or modulation or due to non-immunogenic properties of the cells.

The insulin producing cells of the invention preferably are beta-like cells, i.e. they exhibit characteristics that closely resemble naturally occurring beta-cells. Further, the cells of the invention preferably are capable of a quick response to glucose. After addition of 27.7 mM glucose, the insulin production is enhanced by a factor of at least 2, preferably by a factor of at least 3. Further, the cells of the invention are capable of normalizing blood glucose levels after transplantation into mice.

The invention further encompasses functional pancreatic cells obtainable or obtained by the method according to the invention. The cells are preferably of mammalian, e.g. human origin. Preferably, said cells are pancreatic beta-cells, e.g. mature pancreatic beta-cells or stem cells differentiated into pancreatic beta-cells. Such pancreatic beta cells preferably secrete insulin in response to glucose. Moreover, the present invention provides functional pancreatic cell that express glucagon in response to glucose. A preparation comprising the cells of the invention may additionally contain cells with properties of other endocrine cell types such as alpha-cells, delta-cells and/or PP-cells. These cells are preferably human cells.

The cell preparation of the invention is preferably a pharmaceutical composition comprising the cells together with pharmacologically acceptable carriers, diluents and/or adjuvants. The pharmaceutical composition is preferably used for the treatment or prevention of pancreatic diseases, e.g. diabetes.

According to the present invention, the functional insulin producing cells treated with DG001 may be transplanted preferably intrahepatic, directly into the pancreas of an individual in need, or by other methods. Alternatively, such cells may be enclosed into implantable capsules that can be introduced into the body of an individual, at any location, more preferably in the vicinity of the pancreas, or the bladder, or the liver, or under the skin. Methods of introducing cells into individuals are well known to those of skill in the art and include, but are not limited to, injection, intravenous or parenteral administration. Single, multiple, continuous or intermittent administration can be effected. The cells can be introduced into any of several different sites, including but not limited to the pancreas, the abdominal cavity, the kidney, the liver, the celiac artery, the portal vein or the spleen. The cells may also be deposited in the pancreas of the individual.

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCP Application WO 91/10470 of Aebischer et al., Winn et al., Exper. Neurol., 1 13:322-329, 1991, Aebischer et al., Exper. Neurol., 11 1:269-275, 1991; Tresco et al., ASAIO, 38:17-23, 1992, each of which is specifically incorporated herein by reference. Techniques for formulating a variety of other sustained- or controlled-delivery means, such as liposome carriers, bio-erodible particles or beads and depot injections, are also known to those skilled in the art.

In another embodiment gene therapy ex vivo is carried out, i.e. the patient's own cells are transformed ex vivo to produce a DG001 protein product or a protein stimulating DG001 expression and are directly reimplanted. For example, cells retrieved from the patient are cultured and transformed with an appropriate vector. After an optional propagation/expansion phase, the cells are transplanted back into the same patient's body, particularly the pancreas, where they produce and release the desired DG001 protein product. Delivery by transfection and by liposome injections may be achieved using methods, which are well known in the art. Any of the therapeutic methods described above may be applied to any suitable subject including, for example, mammals such as dogs, cats, cows, horses, rabbits, monkeys, and most preferably, humans.

DG001 product gene therapy in vivo may also be carried out by introducing the gene coding for a DG001 protein product into targeted pancreas cells via local injection of a nucleic acid construct or other appropriate delivery methods (Hefti, J. Neurobiol., 25:1418-1435, 1994). For example, a nucleic acid sequence encoding a DG001 protein product may be cloned to a suitable vector, e.g. an adeno-associated virus vector or adenovirus vector for delivery to the pancreas cells. Alternative viral vectors include, but are not limited to, retrovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

Immunosuppressive drugs, such as cyclosporin, can also be administered to the patient in need to reduce the host reaction versus graft. Allografts using the cells obtained by the methods of the present invention are also useful because a single healthy donor could supply enough cells to regenerate at least partial pancreas function in multiple recipients.

Administration of a DG001 protein product and/or modulators/effectors thereof in a pharmaceutical composition to a subject in need thereof, particularly a human patient, leads to an at least partial regeneration of pancreatic cells. Preferably, these cells are insulin producing beta-cells that will contribute to the improvement of a diabetic state. With the administration of this composition e.g. on a short term or regular basis, an increase in beta-cell mass can be achieved. This effect upon the body reverses the condition of diabetes partially or completely. As the subject's blood glucose homeostasis improves, the dosage administered may be reduced in strength. In at least some cases further administration can be discontinued entirely and the subject continues to produce a normal amount of insulin without further treatment. The subject is thereby not only treated but may be cured entirely of a diabetic condition. Further, beta cells or precursors thereof may be treated in vitro and implanted or reimplanted into a subject in need thereof. Further, other cells of the pancreas can be regenerated in vivo and/or in vitro to cure a certain condition. However, even moderate improvements in beta-cell mass can lead to a reduced requirement for exogenous insulin, improved glycemic control and a subsequent reduction in diabetic complications. In another example, the compositions of the present invention will also have efficacy for treatment of patients with other pancreatic diseases such as pancreatic cancer, dysplasia, or pancreatitis, if beta-cells are to be regenerated.

The nucleic acids of the invention or fragments thereof, may further be useful in diagnostic applications, wherein the presence or amount of the nucleic acids or the proteins are to be assessed. Further antibodies that bind immunospecifically to the novel substances of the invention may be used in therapeutic or diagnostic methods.

For example, in one aspect, antibodies, which are specific for the proteins of the invention and homologous proteins, may be used directly as an effector/modulator, e.g. an antagonist or an agonist, or indirectly as a targeting or delivery mechanism for bringing a pharmaceutical agent to cells or tissue which express the protein. The antibodies may be generated using methods that are well known in the art. Such antibodies may include, but are not limited to, polyclonal, monoclonal, chimeric single chain, Fab fragments, and fragments produced by a Fab expression library. Neutralising antibodies, (i.e., those which inhibit dimer formation) are especially preferred for therapeutic use.

For the production of antibodies, various hosts including goats, rabbits, rats, mice, humans, and others, may be immunized by injection with the protein or any fragment or oligopeptide thereof which has immunogenic properties. Depending on the host species, various adjuvants may be used to increase immunological response. It is preferred that the peptides, fragments or oligopeptides used to induce antibodies to the protein have an amino acid sequence consisting of at least five amino acids, and more preferably at least 10 amino acids.

Monoclonal antibodies to the proteins may be prepared using any technique that provides for the production of antibody molecules by continuous cell lines in culture. These include, but are not limited to, the hybridoma technique, the human B-cell hybridoma technique, and the EBV-hybridoma technique (Köhler, G. and Milstein C., (1975) Nature 256: 495-497; Kozbor, D. et al. (1985) J. Immunol. Methods 81: 31-42; Cote, R. J. et al., (1983) Proc. Natl. Acad. Sci. 80: 2026-2030; Cole, S. P. et al., (1984) Mol. Cell. Biochem. 62: 109-120).

In addition, techniques developed for the production of 'chimeric antibodies', the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al (1984) Nature 312: 604-608; Takeda, S. et al. (1985) Nature 314: 452-454). Alternatively, techniques described for the production of single chain antibodies may be adapted, using methods known in the art, to produce single chain antibodies specific for the proteins of the invention and homologous proteins. Antibodies with related specificity, but of distinct idiotypic composition, may be generated by chain shuffling from random combinatorial immunoglobulin libraries (Kang A. S. et al., (1991) Proc. Natl. Acad. Sci. 88: 11120-11123). Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833-3837; Winter, G. and Milstein C., (1991) Nature 349: 293-299).

Antibody fragments, which contain specific binding sites for the proteins may also be generated. For example, such fragments include, but are not limited to, the $F(ab')_2$ fragments which can be produced by Pepsin digestion of the antibody molecule and the Fab fragments which can be generated by reducing the disulfide bridges of $F(ab')_2$ fragments. Alternatively, Fab expression libraries may be constructed to allow rapid and easy identification of monoclonal Fab fragments with the desired specificity (Huse, W. D. et al. (1989) Science 246:1275-1281).

Various immunoassays may be used for screening to identify antibodies having the desired specificity. Numerous protocols for competitive binding and immunoradiometric assays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering protein epitopes are preferred, but a competitive binding assay may also be employed (Maddox, supra).

In another embodiment of the invention, the polynucleotides or fragments thereof or nucleic acid effector/modulator molecules such as antisense molecules, aptamers, RNAi molecules or ribozymes may be used for therapeutic purposes. In one aspect, aptamers, i.e. nucleic acid molecules, which are capable of binding to a protein of the invention and modulating its activity, may be generated by a screening and selection procedure involving the use of combinatorial nucleic acid libraries.

In a further aspect, antisense molecules may be used in situations in which it would be desirable to block the transcription of the mRNA. In particular, cells may be transformed with sequences complementary to polynucleotides encoding DG001 and homologous proteins. Thus, antisense molecules may be used to modulate/effect protein activity or to achieve regulation of gene function. Such technology is now well known in the art, and sense or antisense oligomers or larger fragments, can be designed from various locations along the coding or control regions of sequences encoding the proteins. Expression vectors derived from retroviruses, adenovirus, herpes or vaccinia viruses or from various bacterial plasmids may be used for delivery of nucleotide sequences to the targeted organ, tissue or cell population. Methods, which are well known to those skilled in the art, can be used to construct recombinant vectors, which will express antisense molecules complementary to the polynucleotides of the genes encoding the proteins of the invention and homologous proteins. These techniques are described both in Sambrook et al. (supra) and in Ausubel et al. (supra). Genes encoding the proteins of the invention and homologous proteins can be turned off by transforming a cell or tissue with expression vectors, which express high levels of polynucleotides that encode the proteins of the invention and homologous proteins or fragments thereof. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or, more with a non-replicating vector and even longer if appropriate replication elements are part of the vector system.

As mentioned above, modifications of gene expression can be obtained by designing antisense molecules, e.g. DNA, RNA or nucleic acid analogues such as PNA, to the control regions of the genes encoding DG001 and homologous proteins, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it cause inhibition of the ability of the double helix to open sufficiently for the binding of polymerases, transcription factors or regulatory molecules. Recent therapeutic advances using triplex DNA have been described in the literature (Gee, J. E. et al., (1994) Gene 149: 109-114; Huber, B. E. and Carr B. I., Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples, which may be used, include engineered hammerhead motif ribozyme molecules that can be specifically and efficiently catalyze endonucleolytic cleavage of sequences encoding the proteins of the invention and homologous proteins. Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Nucleic acid effector/modulator molecules, e.g. antisense molecules and ribozymes may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences. Such DNA sequences may be incorporated into a variety of vectors with suitable RNA polymerase promoters such as T7 or SP6. Alternatively, these cDNA constructs that synthesize antisense RNA constitutively or inducibly can be introduced into cell lines, cells or tissues. RNA molecules may be modified to increase intracellular stability and half-life. Possible modifications include, but are not limited to, the addition of flanking sequences at the 5' and/or 3' ends of the molecule or modifications in the nucleobase, sugar and/or phosphate moieties, e.g. the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods, which are well known in the art. Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of DG001 nucleic acids and the proteins and homologous nucleic acids or proteins, antibodies to the proteins of the invention and homologous proteins, mimetics, agonists, antagonists or inhibitors of the proteins of the invention and homologous proteins or nucleic acids. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone or in combination with other agents, drugs or hormones. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means.

In addition to the active ingredients, these pharmaceutical compositions may contain suitable pharmaceutically-acceptable carriers comprising excipients and auxiliaries, which facilitate processing of the active compounds into preparations, which can be used pharmaceutically. Further details on techniques for formulation and administration may be found in the latest edition of Remington's Pharmaceutical Sciences (Maack Publishing Co., Easton, Pa.).

Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective dose can be estimated initially either in cell culture, assays, e.g., of preadipocyte cell lines or in animal models, usually mice, rabbits, dogs or pigs. The animal model may also be used to determine the appropriate concentration range and route of administration. Such information can then be used to determine useful doses and routes for administration in humans. A therapeutically effective dose refers to that amount of active ingredient, for example the DG001 nucleic acids or proteins or fragments thereof or antibodies, which is sufficient for treating a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week or once every two weeks depending on half-life and clearance rate of the particular formulation. Normal dosage amounts may vary from 0.1 to 100,000 μg, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells, conditions, locations, etc.

In another embodiment, antibodies which specifically bind to the proteins may be used for the diagnosis of conditions or diseases characterized by or associated with over- or underexpression of the proteins of the invention and homologous proteins or in assays to monitor patients being treated with the proteins of the invention and homologous proteins, or effectors/modulators thereof, e.g. agonists, antagonists, or inhibitors. Diagnostic assays include methods which utilize the antibody and a label to detect the protein in human body fluids or extracts of cells or tissues. The antibodies may be used with or without modification, and may be labeled by joining them, either covalently or non-covalently, with a reporter molecule. A wide variety of reporter molecules, which are known in the art may be used several of which are described above.

A variety of protocols including ELISA, RIA, and FACS for measuring proteins are known in the art and provide a basis for diagnosing altered or abnormal levels of gene expression. Normal or standard values for gene expression are established by combining body fluids or cell extracts taken from normal mammalian subjects, preferably human, with antibodies to the protein under conditions suitable for complex formation. The amount of standard complex formation may be quantified by various methods, but preferably by photometric means. Quantities of protein expressed in control and disease, samples e.g. from biopsied tissues are compared with the standard values. Deviation between standard and subject values establishes the parameters for diagnosing disease.

In another embodiment of the invention, the polynucleotides specific for the DG001 proteins and homologous proteins may be used for diagnostic purposes. The polynucleotides, which may be used, include oligonucleotide sequences, antisense RNA and DNA molecules, and PNAs. The polynucleotides may be used to detect and quantitate gene expression in biopsied tissues in which gene expression may be correlated with disease. The diagnostic assay may be used to distinguish between absence, presence, and excess gene expression, and to monitor regulation of protein levels during therapeutic intervention.

In one aspect, hybridization with probes which are capable of detecting polynucleotide sequences, including genomic sequences, encoding the proteins of the invention and homologous proteins or closely related molecules, may be used to identify nucleic acid sequences which encode the respective protein. The hybridization probes of the subject invention may be DNA or RNA and are preferably derived from the nucleotide sequence of the polynucleotide encoding the proteins of the invention or from a genomic sequence including promoter, enhancer elements, and introns of the naturally occurring gene. Hybridization probes may be labeled by a variety of reporter groups; for example, radionuclides such as $^{32}P$ or $^{35}S$ or enzymatic labels, such as alkaline phosphatase coupled to the probe via avidin/biotin coupling systems, and the like.

Polynucleotide sequences specific for DG001 proteins and homologous nucleic acids may be used for the diagnosis of conditions or diseases, which are associated with the expression of the proteins. Examples of such diseases include the pancreatic diseases (e.g. diabetes), obesity, metabolic syndrome, and/or others. Polynucleotide sequences specific for the DG001 proteins and homologous proteins may also be used to monitor the progress of patients receiving treatment for pancreatic diseases (e.g. diabetes), obesity, and/or metabolic syndrome. The polynucleotide sequences may be used qualitative or quantitative assays, e.g. in Southern or Northern analysis, dot blot or other membrane-based technologies; in PCR technologies; or in dip stick, pin, ELISA or chip assays utilizing fluids or tissues from patient biopsies to detect altered gene expression.

In a particular aspect, the DG001 nucleotide sequences may be useful in assays that detect activation or induction of various metabolic diseases or dysfunctions. The nucleotide sequences may be labeled by standard methods, and added to a fluid or tissue sample from a patient under conditions suitable for the formation of hybridization complexes. After a suitable incubation period, the sample is washed and the signal is quantitated and compared with a standard value. The presence of altered levels of nucleotide sequences encoding the proteins of the invention and homologous proteins in the sample indicates the presence of the associated disease. Such assays may also be used to evaluate the efficacy of a particular therapeutic treatment regimen in animal studies, in clinical trials or in monitoring the treatment of an individual patient.

In order to provide a basis for the diagnosis of a disease associated with expression of the DG001 proteins and homologous proteins, a normal or standard profile for expression is established. This may be accomplished by combining body fluids or cell extracts taken from normal subjects, either animal or human, with a sequence or a fragment thereof, which is specific for the nucleic acids encoding the proteins of the invention and homologous nucleic acids, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease. Once disease is established and a treatment protocol is initiated, hybridization assays may be repeated on a regular basis to evaluate whether the level of expression in the patient begins to approximate that, which is observed in the normal patient. The results obtained from successive assays may be used to show the efficacy of treatment over a period ranging from several days to months.

With respect to pancreatic diseases (e.g. diabetes), obesity, and/or metabolic syndrome, the presence of an unusual amount of transcript in biopsied tissue from an individual may indicate a predisposition for the development of the disease or may provide a means for detecting the disease prior to the appearance of actual clinical symptoms. A more definitive diagnosis of this type may allow health professionals to employ preventative measures or aggressive treatment earlier thereby preventing the development or further progression of the metabolic diseases and disorders.

Additional diagnostic uses for oligonucleotides designed from the sequences encoding the proteins of the invention and homologous proteins may involve the use of PCR. Such oligomers may be chemically synthesized, generated enzymatically or produced from a recombinant source. Oligomers will preferably consist of two nucleotide sequences, one with sense orientation (5prime.fwdarw.3prime) and another with antisense (3prime.rarw.5prime), employed under optimized conditions for identification of a specific gene or condition. The same two oligomers, nested sets of oligomers or even a degenerate pool of oligomers may be employed under less stringent conditions for detection and/or quantification of closely related DNA or RNA sequences.

In another embodiment of the invention, the nucleic acid sequences may also be used to generate hybridization probes, which are useful for mapping the naturally occurring genomic sequence. The sequences may be mapped to a particular chromosome or to a specific region of the chromosome using well known techniques. Such techniques include FISH, FACS or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127-134, and Trask, B. J. (1991) Trends Genet. 7:149-154. FISH (as described in Verma et al. (1988) Human Chromosomes: A Manual of Basic Techniques, Pergamon Press, New York, N.Y.). The results may be correlated with other physical chromosome mapping techniques and genetic map data. Examples of genetic map data can be found in the 1994 Genome Issue of Science (265:1981f). Correlation between the location of the gene encoding the proteins of the invention on a physical chromosomal map and a specific disease or predisposition to a specific disease, may help to delimit the region of DNA associated with that genetic disease.

The nucleotide sequences of the subject invention may be used to detect differences in gene sequences between normal, carrier or affected individuals. An analysis of polymorphisms, e.g. single nucleotide polymorphisms may be carried out. Further, in situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336: 577-580), any sequences mapping to that area may represent associated or regulatory genes for further investigation. The nucleotide sequences of the subject invention may also be used to detect differences in the chromosomal location due to translocation, inversion, etc. among normal, carrier or affected individuals.

In another embodiment of the invention, the proteins of the invention, their catalytic or immunogenic fragments or oligopeptides thereof, an in vitro model, a genetically altered cell or animal, can be used for screening libraries of compounds in any of a variety of drug screening techniques. One can identify effectors, e.g. receptors, enzymes, proteins, ligands, or substrates that bind to, modulate or mimic the action of one or more of the DG001 proteins of the invention. The protein or fragment thereof employed in such screening may be free in solution, affixed to a solid support, borne on a cell surface, or located intracellulary. The formation of binding complexes, between the DG001 proteins of the invention and the agent tested, may be measured. Agents could also, either directly or indirectly, influence the activity of the proteins of the invention.

In addition activity of the proteins of the invention against their physiological substrate(s) or derivatives thereof could be measured in cell-based or cell-free assays. Agents may also interfere with posttranslational modifications of the protein, such as phosphorylation and dephosphorylation, farnesylation, palmitoylation, acetylation, alkylation, ubiquitination, proteolytic processing, subcellular localization and degradation. Moreover, agents could influence the dimerization or oligomerization of the proteins of the invention or, in a heterologous manner, of the proteins of the invention with other proteins, for example, but not exclusively, docking proteins, enzymes, receptors, or translation factors. Agents could also act on the physical interaction of the proteins of this invention with other proteins, which are required for protein function, for example, but not exclusively, their downstream signaling.

Methods for determining protein-protein interaction are well known in the art. For example binding of a fluorescently labeled peptide derived from the interacting protein to the DG001 protein of the invention, or vice versa, could be detected by a change in polarisation. In case that both binding partners, which can be either the full length proteins as well as one binding partner as the full length protein and the other just represented as a peptide are fluorescently labeled, binding could be detected by fluorescence energy transfer (FRET) from one fluorophore to the other. In addition, a variety of commercially available assay principles suitable for detection of protein-protein Interaction are well known In the art, for example but not exclusively, AlphaScreen (PerkinElmer) or Scintillation Proximity Assays (SPA) by Amersham. Alternatively, the interaction of the DG001 proteins of the invention with cellular proteins could be the basis for a cell-based screening assay, in which both proteins are fluorescently labeled and interaction of both proteins is detected by analysing cotranslocation of both proteins with a cellular imaging reader, as has been developed for example, but not exclusively, by Cellomics or EvotecOAl. In all cases the two or more binding partners can be different proteins with one being the protein of the invention, or in case of dimerization and/or oligomerization the protein of the invention itself.

Of particular interest are screening assays for agents that have a low toxicity for mammalian cells. The term "agent" as used herein describes any molecule, e.g. protein or pharmaceutical, with the capability of altering or mimicking the physiological function of one or more of the proteins of the invention. Candidate agents encompass numerous chemical classes, though typically they are organic molecules, preferably small organic compounds having a molecular weight of more than 50 and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Candidate agents are also found among biomolecules including peptides, saccharides, fatty acids, steroids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Where the screening assay is a binding assay, one or more of the molecules may be joined to a label, where the label can directly or indirectly provide a detectable signal.

Another technique for drug screening, which may be used, provides for high throughput screening of compounds having suitable binding affinity to the protein of interest as described in published PCT application WO 84/03564. In this method, as applied to the proteins of the invention large numbers of different small test compounds, e.g. aptamers, peptides, low-molecular weight compounds etc., are provided or synthesized on a solid substrate, such as plastic pins or some other surface. The test compounds are reacted with the proteins or fragments thereof, and washed. Bound proteins are then detected by methods well known in the art. Purified proteins can also be coated directly onto plates for use in the aforementioned drug screening techniques. Alternatively, non-neutralizing antibodies can be used to capture the peptide and immobilize it on a solid support. In another embodiment, one may use competitive drug screening assays in which neutralizing antibodies capable of binding the protein specifically compete with a test compound for binding the protein. In this manner, the antibodies can be used to detect the presence of any peptide, which shares one or more antigenic determinants with the protein.

Compounds that bind DG001 proteins, e.g. antibodies, are useful for the identification or enrichment of cells, which are positive for the expression of the proteins of the invention, from complex cell mixtures. Such cell populations are useful in transplantation, for experimental evaluation, and as source of lineage and cell specific products, including mRNA species useful in identifying genes specifically expressed in these cells, and as target for the identification of factors of molecules that can affect them. Cells expressing the protein of the invention or which have been treated with the protein of the invention are useful in transplantation to provide a recipient with pancreatic islet cells, including insulin producing beta cells; for drug screening; experimental models of islet differentiation and interaction with other cell types; in vitro screening assays to define growth and differentiation factors, and to additionally characterize genes involved in islet development and regulation; and the like. The native cells may be used for these purposes, or they may be genetically modified to provide altered capabilities. Cells from a regenerating pancreas, from embryonic foregut, stomach and duodenum, or other sources of pancreatic progenitor cells may be used as a starting population. The progenitor cells may be obtained from any mammalian species, e.g. equine, bovine, porcine, canine, feline, rodent, e.g. mice, rats, hamster, primate, etc. particularly human.

In another embodiment, in a high-throughput screening method, the cells are transfected with a DNA construct, e.g. a viral or non-viral vector containing a reporter gene, e.g. the lacZ gene or the GFP gene, under regulatory control of a promoter of a gene involved in for example beta-cell differentiation, e.g. a promoter of a gene stimulation beta-cell differentiation, preferably a Pax4 promoter. The transfected cells are divided into aliquots and each aliquot is contacted with a test substance, e.g., DG001. The activity of the reporter gene corresponds to the capability of the test compound to induce beta-cell differentiation.

In a further embodiment, which may be combined with the high-throughput screening as described above, a medium throughput validation is carried out. Therein, the test compound is added to stem cells being cultivated and the insulin production, is determined. Following an initial high throughput assay, such as the cell based assay outlined above where for example a Pax4 promoter is used as marker for beta-cell regeneration, the activity of candidate molecules to induce beta-cell differentiation is tested in a validation assay comprising adding said compounds to the culture media of the embryoid bodies. Differentiation into insulin-producing cells is then evaluated, e.g. by comparison to wild type and/or Pax4 expressing ES cells to assess the effectiveness of a compound.

The nucleic acids encoding the DG001 proteins of the invention can be used to generate transgenic cell lines and animals. These transgenic non-human animals are useful in the study of the function and regulation of the proteins of the invention in vivo. Transgenic animals, particularly mammalian transgenic animals, can serve as a model system for the investigation of many developmental and cellular processes common to humans. A variety of non-human models of metabolic disorders can be used to test modulators of the protein of the invention. Misexpression (for example, over-expression or lack of expression) of the protein of the invention, particular feeding conditions, and/or administration of biologically active compounds can create models of metabolic disorders.

In one embodiment of the invention, such assays use mouse models of insulin resistance and/or diabetes, such as mice carrying gene knockouts in the leptin pathway (for example, ob (leptin) or db (leptin receptor) mice), as described above. In addition to testing the expression of the proteins of the invention in such mouse strains (see Examples), these mice could be used to test whether administration of a candidate modulator alters for example lipid accumulation in the liver, in plasma, or adipose tissues using standard assays well known in the art, such as FPLC, colorimetric assays, blood glucose level tests, insulin tolerance tests and others.

Transgenic animals may be made through homologous recombination in non-human embryonic stem cells, where the normal locus of the gene encoding the protein of the invention is altered. Alternatively, a nucleic acid construct encoding the protein of the invention is injected into oocytes and is randomly integrated into the genome. Vectors for stable integration include plasmids, retroviruses and other animal viruses, yeast artificial chromosomes (YACs), and the like. The modified cells or animals are useful in the study of the function and regulation of the protein of the invention. For example, a series of small deletions and/or substitutions may be made in the gene that encodes the protein of the invention to determine the role of particular domains of the protein, functions in pancreatic differentiation, etc.

Furthermore, variants of the genes of the invention like specific constructs of interest include anti-sense molecules, which will block the expression of the protein of the invention, or expression of dominant negative mutations, which will block or alter the expression of the proteins of the invention may be randomly integrated into the genome. A detectable marker, such as lac Z or luciferase may be introduced into the locus of the genes of the invention, where upregulation of expression of the genes of the invention will result in an easily detected change in phenotype.

One may also provide for expression of the genes of the invention or variants thereof in cells or tissues where it is not normally expressed or at abnormal times of development. In addition, by providing expression of the protein of the invention in cells in which they are not normally produced, one can induce changes in cell behavior.

DNA constructs for homologous recombination will comprise at least portions of the genes of the invention with the desired genetic modification, and will include regions of homology to the target locus. DNA constructs for random integration do not need to contain regions of homology to mediate recombination. Conveniently, markers for positive and negative selection are included. DNA constructs for random integration will consist of the nucleic acids encoding the proteins of the invention, a regulatory element (promoter), an intron and a poly-adenylation signal. Methods for generating cells having targeted gene modifications through homologous recombination are known in the art. For non-human embryonic stem (ES) cells, an ES cell line may be employed, or embryonic cells may be obtained freshly from a host, e.g. mouse, rat, guinea pig, etc. Such cells are grown on an appropriate fibroblast-feeder layer and are grown in the presence of leukemia inhibiting factor (LIF).

When non-human ES or embryonic cells or somatic pluripotent stem cells have been transfected, they may be used to produce transgenic animals. After transfection, the cells are plated onto a feeder layer in an appropriate medium. Cells containing the construct may be selected by employing a selection medium. After sufficient time for colonies to grow, they are picked and analyzed for the occurrence of homologous recombination or integration of the construct. Colonies that are positive may then be used for embryo manipulation and morula aggregation. Briefly, morulae are obtained from 4 to 6 week old superovulated females, the Zona Pellucida is removed and the morulae are put into small depressions of a tissue culture dish. The ES cells are trypsinized, and the modified cells are placed into the depression closely to the morulae. On the following day the aggregates are transferred into the uterine horns of pseudopregnant females. Females are then allowed to go to term. Chimeric offsprings can be readily detected by a change in coat color and are subsequently screened for the transmission of the mutation into the next generation (F1-generation). Offspring of the F1-generation are screened for the presence of the modified gene and males and females having the modification are mated to produce homozygous progeny. If the gene alterations cause lethality at some point in development; tissues or organs can be maintained as allogenic or congenic grafts or transplants, or in vitro culture. The transgenic animals may be any non-human mammal, such as laboratory animal, domestic animals, etc., for example, mouse, rat, guinea pig, sheep, cow, pig, and others. The transgenic animals may be used in functional studies, drug screening, and other applications and are useful in the study of the function and regulation of the proteins of the invention in vivo.

Finally, the invention also relates to a kit comprising at least one of
(a) a nucleic acid molecule coding for a protein of the invention or a functional fragment thereof;
(b) a protein of the invention or a fragment or an isoform thereof;
(c) a vector comprising the nucleic acid of (a);
(d) a host cell comprising the nucleic acid of (a) or the vector of (c);
(e) a polypeptide encoded by the nucleic acid of (a) or the vector of (c);
(f) a fusion polypeptide encoded by the nucleic acid of (a) or the vector of (c);
(g) an antibody, an aptamer or another effector/modulator against the nucleic acid of (a) or the polypeptide of (b), (e) or (f) and
(h) an anti-sense oligonucleotide of the nucleic acid of (a).

The kit may be used for diagnostic or therapeutic purposes or for screening applications as described above. The kit may further contain user instructions.

The Figures show:

FIG. 1 shows human DG001 nucleic acid and protein.

FIG. 1A shows the nucleic acid sequence encoding the human DG001 protein (SEQ ID NO: 1).

FIG. 1B shows the amino acid sequence (one-letter code) of human DG001 protein (SEQ ID NO: 2).

FIG. 2 shows the analysis of DG001 protein expression in mammalian tissues. The relative RNA-expression is shown on the Y-axis, in FIG. 2A to 2C the tissues tested are given on the X-axis. WAT refers to white adipose tissue, BAT refers to brown adipose tissue. In FIG. 2D, the X-axis represents the time axis. 'd0' refers to day 0 (start of the experiment), 'd2'-'d12' refers to day 2 day 12 of adipocyte differentiation).

Figure 2A:
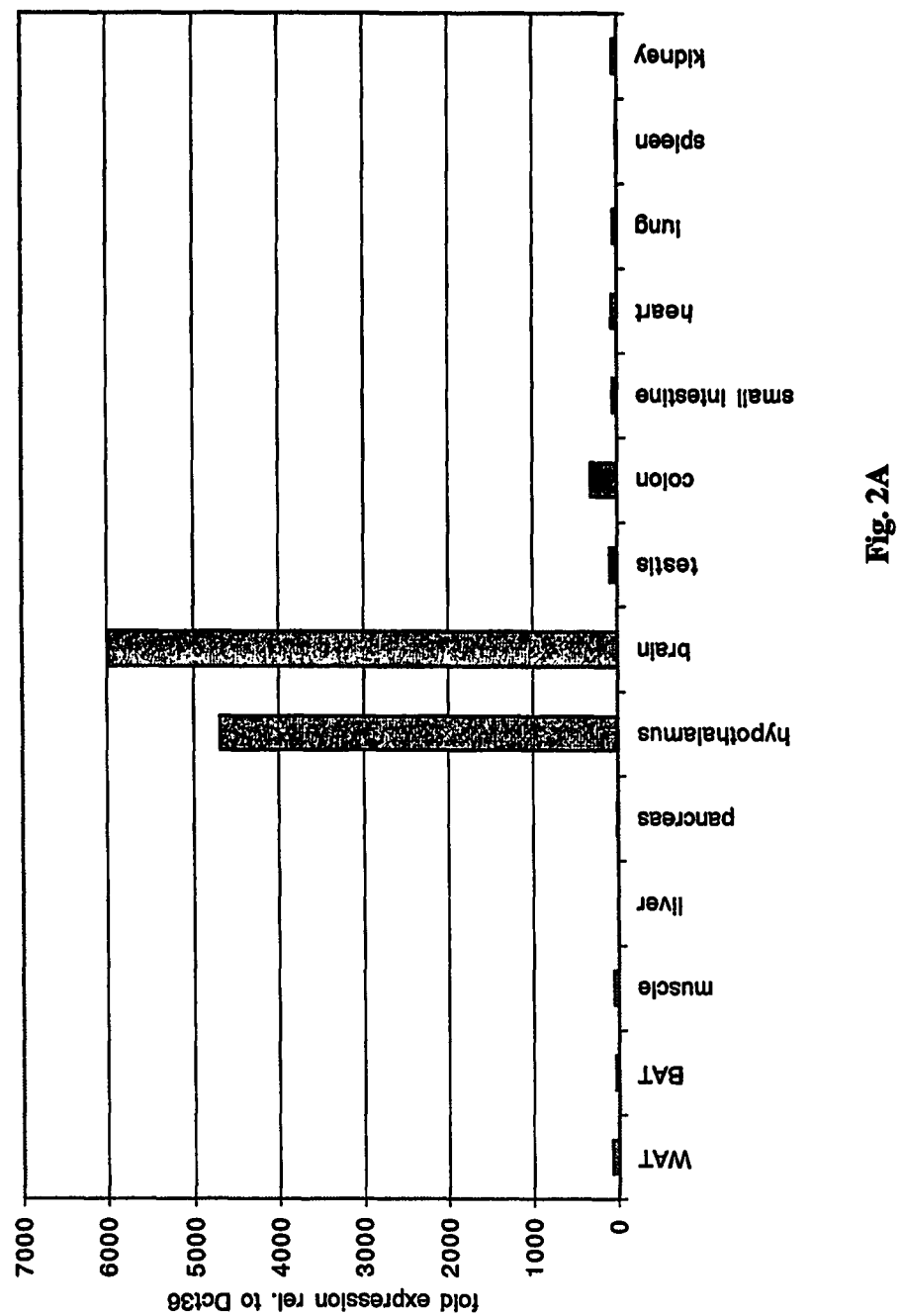

FIG. 2A shows the quantitative (real-time PCR) analysis of DG001 expression in wild-type mouse tissues.

Figure 2B:
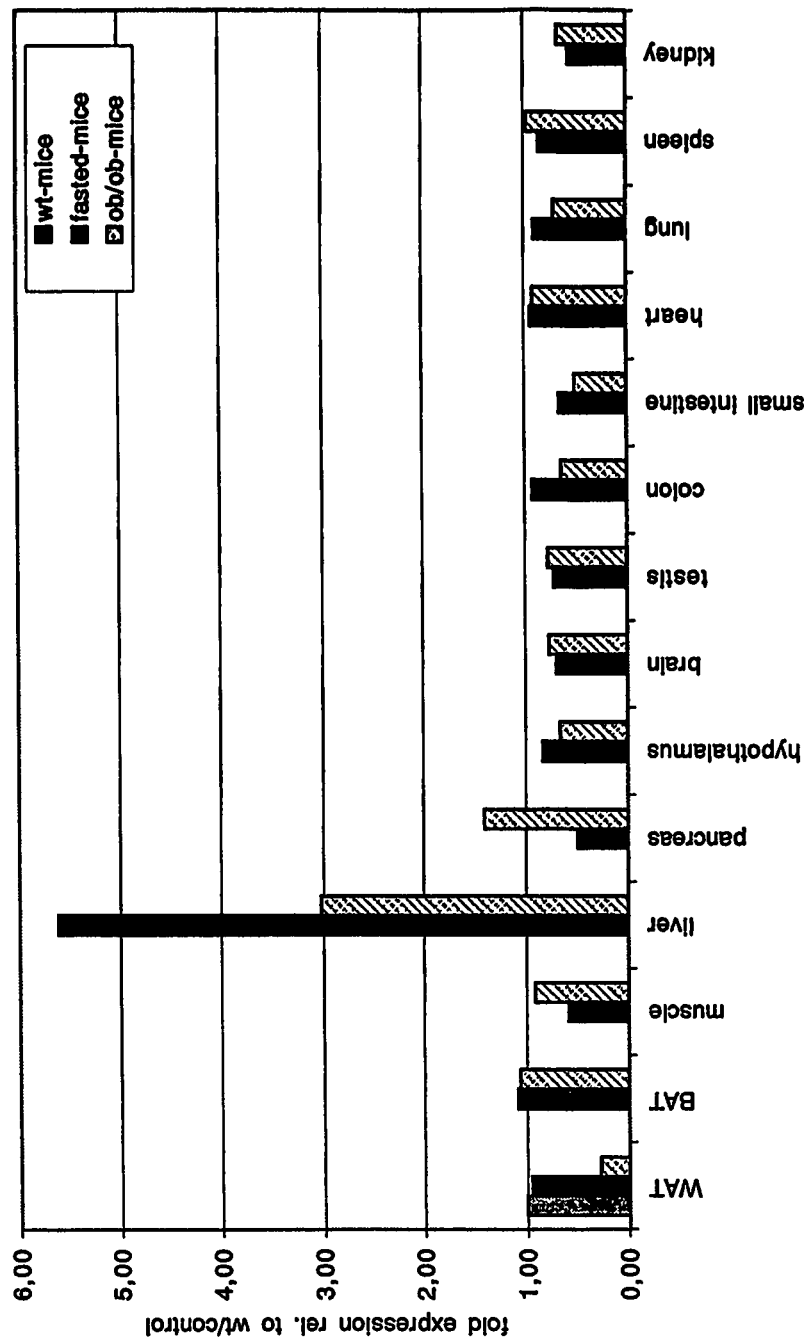

FIG. 2B shows the quantitative (real-time PCR) analysis of DG001 expression in genetically obese mice (ob/ob-mice) and fasted mice (fasted-mice) compared to wild-type mice (wt-mice).

Figure 2C:
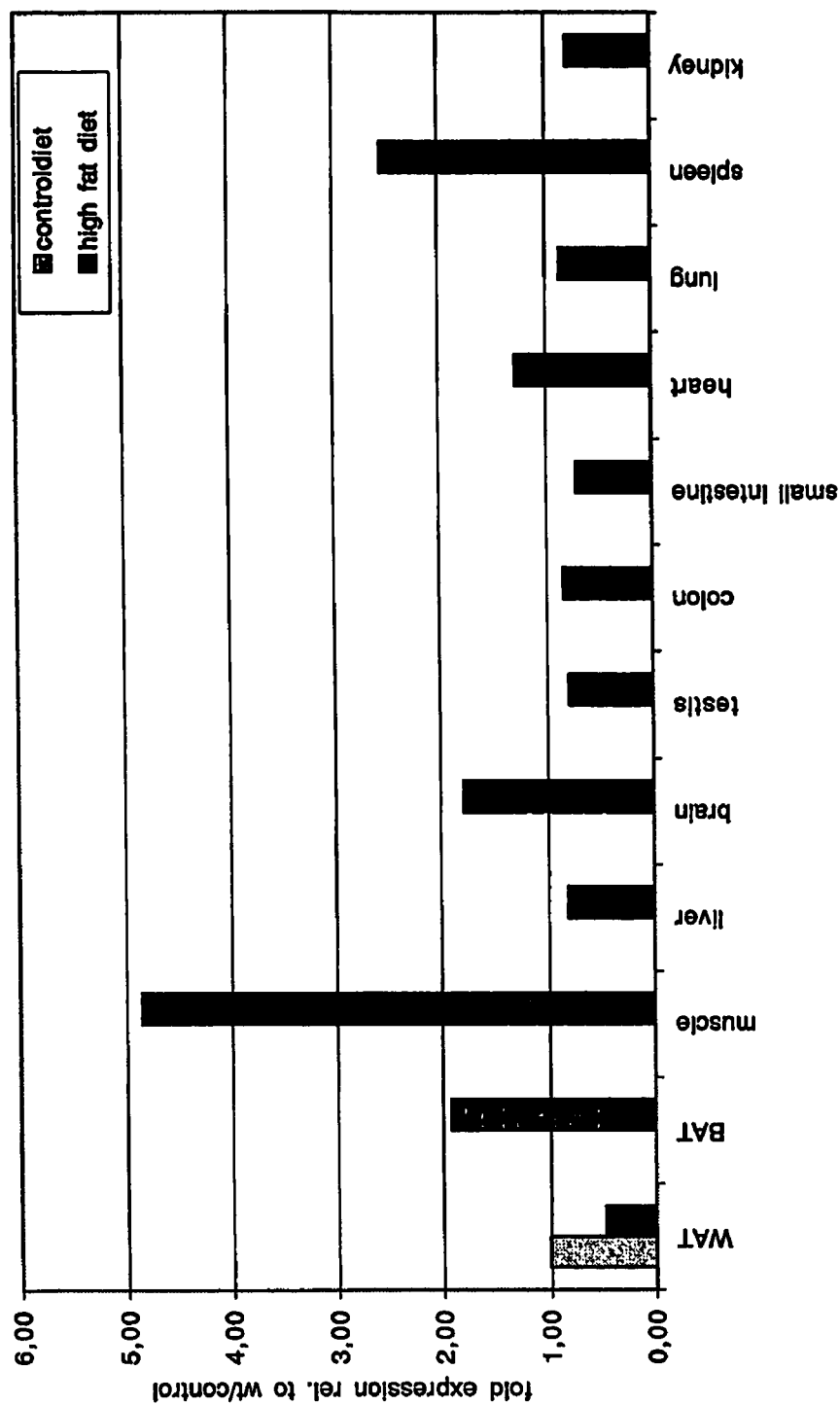

FIG. 2C shows the quantitative (real-time PCR) analysis of DG001 expression in mice fed with a high fat diet compared to mice fed with a control diet.

Figure 2D:
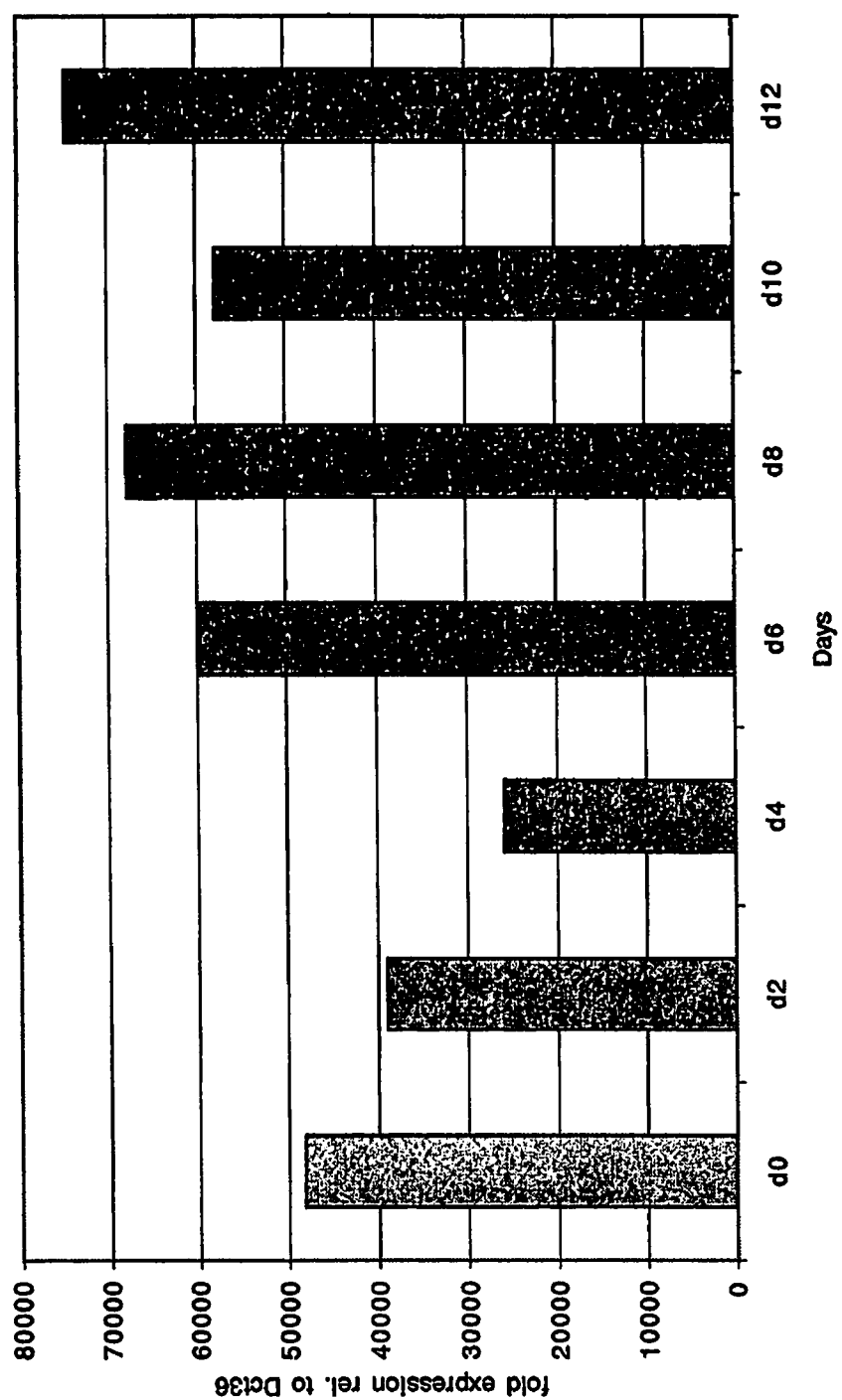

FIG. 2D shows the quantitative (real-time PCR) analysis of DG001 expression in mammalian fibroblast (3T3-L1) cells, during the differentiation from preadipocytes to mature adipocytes.

Figure 2E:
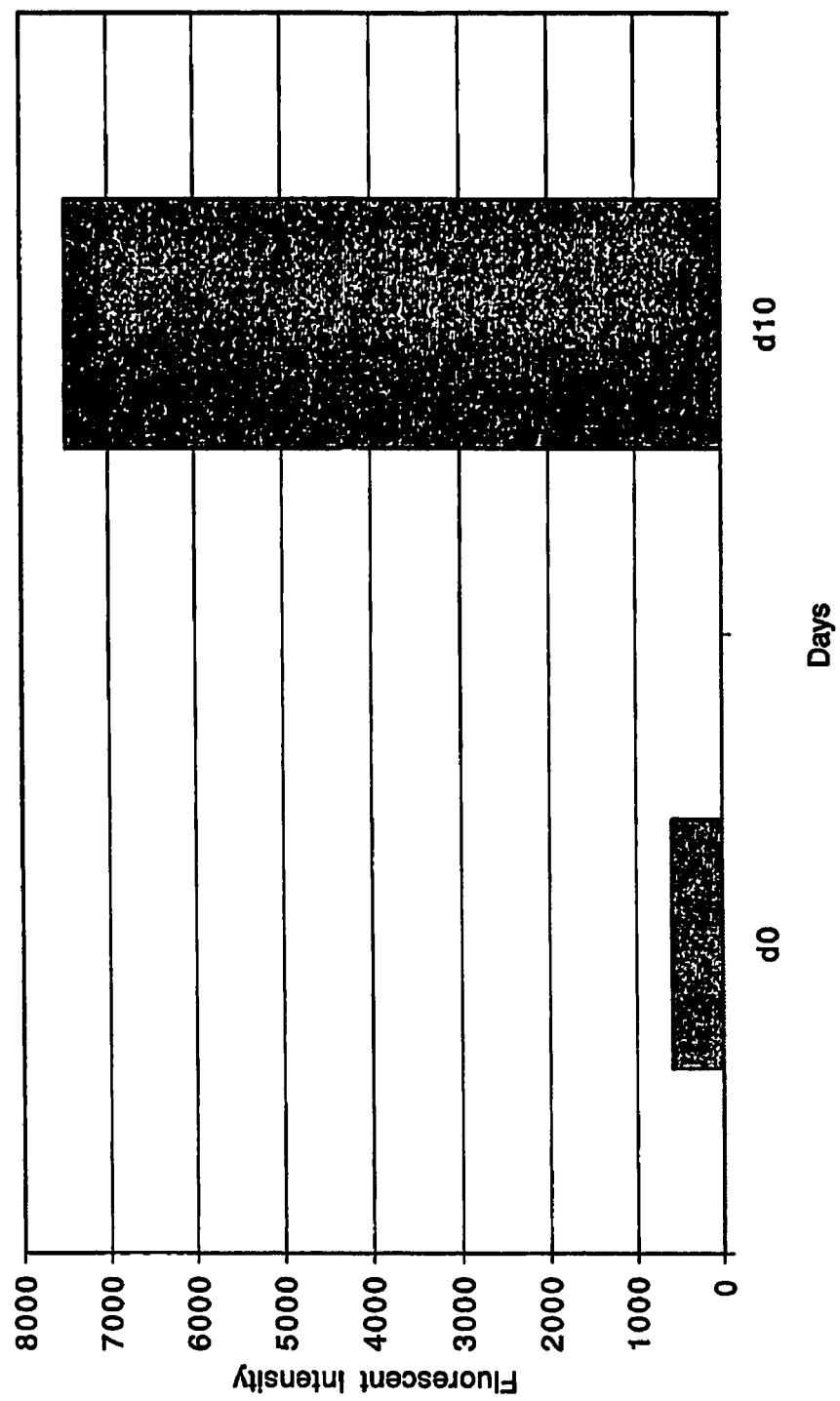

FIG. 2E shows the microarray analysis of DG001 expression in mammalian fibroblast (3T3-L1) cells, during the differentiation from preadipocytes to mature adipocytes.

Figure 3:
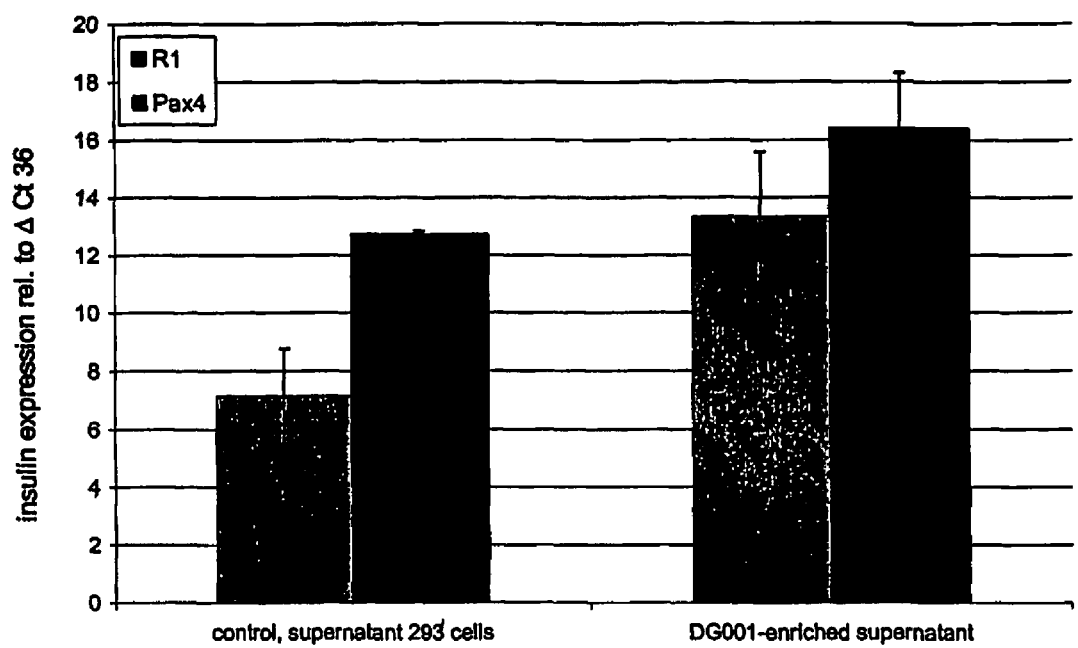

FIG. 3 shows the DG001 dependent induction of the differentiation of insulin producing cells.

Mouse embryonic stem (ES) cells were differentiated as described previously (patent application PCT/EP02/04362, published as WO 02/086107, which is incorporated herein by reference). At the end of the differentiation procedure, cells were harvested and total RNA was isolated. The abundance of insulin mRNA (FIG. 3) was determined using quantitative RT-PCR in an Applied Biosystems 7000 sequence detection device. Levels were normalized using 18S RNA as control and a cycle number of 36 as reference. The numbers on the vertical line refer to the abundance of the indicated transcripts relative to an abundance for which 36 cycles are necessary for detection. 'R1' refers to unmodified mouse R1 embryonic stem (ES) cells; 'Pax4' refers to R1 mouse embryonic stem (ES) cells stably transfected with a CMV-Pax4 expression construct; insulin expression rel. to 'ΔCt36' refers to expression of insulin in FIG. 3; 'control, supernatant 293 cells' refers to the differentiation protocol as described in Example 6, with the addition of supernatant of 293 cells without DG001; 'DG001-enriched supernatant' refers to the differentiation protocol as described in Example 7, with the addition of DG001 enriched supernatant of 293 cells to differentiated cells.

The examples illustrate the invention:

EXAMPLE 1

Identification of Secreted Factors Expressed in Pancreas

A screen for secreted factors expressed in developing mouse pancreas was carried out according to methods known by those skilled, in the art (see, for example Pera E. M. and De Robertis E. M., (2000) Mech Dev 96: 183-195) with several modifications.

Expression cDNA Library:

During organogenesis, the pancreatic bud is surrounded and influenced by the associated mesenchyme. (see for example, Madsen O. D. et al., (1996) Eur. J. Biochem. 242: 435-445 and Slack, J. M., (1995) Development 121: 1569-1580). Recently, it was suggested, that white adipocytes origin directly from mesenchymal cells (Atanossova P. K., (2003) Folia Med. 45: 41-45). During embryogenesis, the innervation and vascularization of the pancreas can be observed. Therefore, the tissue used in the screen might have contained besides pancreatic cells some adipocyte precursors, blood vessels, as well as neuronal cells.

A mouse embryonic stage 9.5-15 pancreatic bud library was prepared in pCMVSPORT-6 vector using SUPER-SCRIPT Plasmid System from Invitrogen according to the manufacturer's instructions. The non-amplified library was electroporated into MaxEff DH10B cells (Invitrogen).

Secretion Cloning

Bacterial clones were picked with sterile toothpicks from agar plates and cultured in 96-deep-well microtiter plates in LB-ampicillin (see Sambrook et al., supra). Aliquots of 8 cultures were pooled, and plasmid DNA was isolated using the BioRobot_9600 apparatus according to the manufacturer's instructions (Qiagen; QIAprep(r) Turbo BioRobot Kit. Human 293 cell culture cells were cultured in 75 ml tissue culture flasks in DMEM and 10% fetal calf serum. At 90-99% confluence, the cells were splitted at 1:3 ratio and plated onto poly-D-lysine (Sigma) coated 96-well plates. Cells were transfected with 100-500 ng plasmid using lipofectamine 2000 (Invitrogen). After 6 hours, the medium was exchanged for fresh complete growth medium. 24 hours after transfection, the cells were washed twice with DMEM without cysteine and methionine (Invitrogen), supplemented with 1% dialysed Bovine serum (Sigma) with 50 microgram per ml Heparin (Sigma) and glutamine. The cells were labeled radio-actively ('S35 Met-label', from Hartmann Analytic GmbH). After 12 hours, aliquots of the supernatants were harvested in 96-well PCR plates and subjected to SDS gel electrophoresis in precast 4∇20% gradient polyacrylamide Criterion gels (Biorad) under reducing conditions, using Criterion Dodeca Cell gel running chamber (Biorad). The gels were fixed in 10% acetic acid, 25% isopropanol for 30 min, soaked 15-30 min in AMPLIFY reagent (Amersham), dried and exposed to X-OMAT (AR) film (Kodak). Positive clones were identified and regrown in 96-well-plates. DNA of individual clones was prepared and used for transfection as described above. If one of the clones yielded proteins of the same size as that of the original pool, a positive clone was identified. Positive clones were partially sequenced from the 5prime end (SEQLAB, Goettingen).

EXAMPLE 2

Identification of the Human DG001 Homologous Nucleic Acid And Protein

The term "polynucleotide comprising the nucleotide sequence as shown in GenBank Accession number" relates to the expressible gene of the nucleotide sequences deposited under the corresponding GenBank Accession number. The term "GenBank Accession number" relates to NCBI GenBank database entries (Ref.: Benson et al., Nucleic Acids Res. 28 (2000) 15-18).

DG001 homologous proteins and nucleic acid molecules coding therefore are obtainable from insect or vertebrate species, e.g. mammals or birds. Particularly preferred are nucleic acids comprising human DG001 homologs. The following mouse sequence was identified in the secreted factor screen: GenBank Accession Number NM_008973 and GenBank Accession Number NP_032999.

Sequences homologous to mouse DG001 were identified using the publicly available program BLASTP 2.2.3 of the non-redundant protein data base of the National Center for Biotechnology Information (NCBI) (see, Altschul et al., 1997, Nucleic Acids Res. 25: 3389-3402). The best human homolog of mouse DG001 is GenBank Accession Number NM_002825 (SEQ ID NO: 1; see FIG. 1A) and GenBank Accession Number NP_002816 (SEQ ID NO: 2; see FIG. 1B).

EXAMPLE 3

Expression of the Polypeptides in Mammalian Tissues

To analyse the expression of the polypeptides disclosed in this invention in mammalian tissues, several mouse strains (preferably mice strains C57Bl/6J, C57Bl/6 ob/ob and C57Bl/KS db/db which are standard model systems in obesity and diabetes research) were purchased from Harlan Winkelmann (33178 Borchen, Germany) and maintained under constant temperature (preferably 22YC), 40 percent humidity and a light/dark cycle of preferably 14/10 hours. The mice were fed a standard chow (for example, from ssniff Spezialitäten GmbH, order number ssniff M-Z V1126-000). For the fasting experiment ("fasted wild-type mice"), wild-type mice were starved for 48 h without food, but only water supplied ad libitum (see, for example, Schnetzler et al., (1993) J Clin Invest 92: 272-280, Mizuno et al. (1996) Proc Natl Acad Sci 93: 3434-3438). In a further experiment wild-type (wt) mice were fed a control diet (preferably Altromin C1057 mod control, 4.5% crude fat) or high fat diet (preferably Altromin C1057 mod. high fat, 23.5% crude fat). Animals, were sacrificed at an age of 6 to 8 weeks. The animal tissues, were isolated according to standard procedures known to those skilled in the art, snap frozen in liquid nitrogen and stored at −80° C. until needed.

For analyzing the role of the proteins disclosed in this invention in the in vitro differentiation of different mammalian cell culture cells for the conversion of pre-adipocytes to adipocytes, mammalian fibroblast (3T3-L1) cells (e.g., Green & Kehinde, (1974) Cell 1: 113-116) were obtained from the American Tissue Culture Collection (ATCC, Hanassas, Va., USA; ATCC-CL 173). 3T3-L1 cells were maintained as fibroblasts and differentiated into adipocytes as described in the prior art (e.g., Qiu. et al., (2001) J. Biol. Chem. 276: 11988-11995; Slieker et al., (1998) BBRC 251: 225-229). In brief, cells were plated in DMEM/10% FCS (Invitrogen, Karlsruhe, Germany) at 50,000 cells/well in duplicates in 6-well plastic dishes and cultured in a humidified atmosphere of 5% $CO_2$ at 37° C. At confluence (defined as day 0: d0) cells were transferred to serum-free (SF) medium, containing DMEM/HamF12 (3:1; Invitrogen), fetuin (300 µg/ml; Sigma, Munich, Germany), transferrin (2 µg/ml; Sigma), pantothenate (17 µM; Sigma), biotin (1 µM; Sigma), and EGF (0.8 nM; Hoffmann-La Roche, Basel, Switzerland). Differentiation was induced by adding dexamethasone (DEX; 1 µM; Sigma), 3-methyl-isobutyl-1-methylxanthine (MIX; 0.5 mM; Sigma), and bovine insulin (5 µg/ml; Invitrogen). Four days after confluence (d4), cells were kept in SF medium, containing bovine insulin (5 µg/ml) until differentiation was completed. At various time points of the differentiation procedure, beginning with day 0 (day of confluence) and day 2 (hormone addition; for example, dexamethasone and 3-isobutyl-1-methylxanthine), up to 10 days of differentiation, suitable aliquots of cells were taken every two days.

RNA was isolated from mouse tissues or cell culture cells using Trizol Reagent (for example, from Invitrogen, Karlsruhe, Germany) and further purified with the RNeasy Kit (for example, from Qiagen, Germany) in combination with an DNase-treatment according to the instructions of the manufacturers and as known to those skilled in the art. Total RNA was reverse transcribed (preferably using Superscript II RNaseH—Reverse Transcriptase, from Invitrogen, Karlsruhe, Germany) and subjected to Taqman analysis preferably using the Taqman 2×PCR Master Mix (from Applied Biosystems, Weiterstadt, Germany; the Mix contains according to the Manufacturer for example AmpliTaq Gold DNA Polymerase, AmpErase UNG, dNTPs with dUTP, passive reference Rox and optimized buffer components) on a Gene-Amp 5700 Sequence Detection System (from Applied Biosystems, Weiterstadt, Germany).

The following primer/probe combinations were used for the TaqMan analysis (GenBank Accession Number NM_008973 for the mouse DG001 sequence): Mouse DG001 forward primer (Seq ID NO: 3): 5'-CAA GTA CCA GTT CCA GGC TTG G-3'; mouse DG001 reverse primer (Seq ID NO: 4): 5'-GCT CGC TTC AGG CTG CC-3'; mouse DG001 Taqman probe (Seq ID NO: 5):

```
(5/6-FAM) TGA CCT CAA TAC CGC CTT GAA GAC CAG AAC
(5/6-TAMRA).
```

The function of the mammalian DG001 in metabolism was further validated by analyzing the expression of the transcripts in different tissues and by analyzing the role in adipocyte differentiation.

Expression profiling studies confirm the particular relevance of DG001 as regulator of energy metabolism in mammals. Quantitative PCR (Taqman) analysis revealed that DG001 is expressed in several mammalian tissues, with highest expression levels in hypothalamus and brain in wild type mice. In 5, addition, DG001 is expressed in metabolic active tissue such as white adipose tissue (WAT) and at lower levels in brown adipose tissue (BAT) in wild type mice as depicted in FIG. 2A.

We used mouse models of insulin resistance and/or diabetes, such as mice carrying gene knockouts in the leptin pathway (for example, ob/ob (leptin) or db (leptin receptor/ligand) mice) to study the expression of DG001. Such mice develop typical symptoms of diabetes, show hepatic lipid accumulation and frequently have increased plasma lipid levels (see Bruning et al, (1998) Mol. Cell. 2: 559-569). We found, for example, that the expression of DG001 is down-regulated in metabolic active tissue (WAT) in genetically induced obese mice (ob/ob) compared to wild type mice and strongly up-regulated in liver in genetically induced obese mice (ob/ob) and fasted mice compared to wild type mice (see FIG. 2B).

Expression of DG001 mRNA was also examined in susceptible wild type mice (for example, C57Bl/6) that show symptoms of diabetes, lipid accumulation, and high plasma lipid levels, if fed a high fat diet. In those mice, the expression of DG001 is down-regulated in WAT and up-regulated in spleen and muscle supporting that DG001 is involved in the regulation of mammalian metabolism (see FIG. 2C).

We show in this invention that the DG001 mRNA is decreased at a very early stage of adipose differentiation (until day 4) and increased during the late stage of differentiation into mature adipocytes (FIG. 2D). Therefore, the DG001 protein might play an essential role in adipogenesis.

EXAMPLE 4

Microarray Analysis of the Differential Expression of Transcripts of the Proteins of the Invention in Mammalian Tissues RNA preparation from murine 3T3-L1 cells was done as described in Example 3. The target preparation, hybridization, and scanning was performed as described in the manufactures manual (see Affymetrix Technical Manual, 2002, obtained from Affmetrix, Santa Clara, USA).

The expression analysis (using Affymetrix GeneChips) of the DG001 gene using 3T3-L1 differentiation clearly shows an up-regulation of human. DG001 in adipocytes, confirming the 3T3-L1 differentiation data obtained with the TaqMan method described in Example 3.

EXAMPLE 5

Generation of ES Cells Expressing the Pax4 Gene

Mouse R1 ES cells (Nagy et al., (1993) Proc. Natl. Acad. Sci. USA 90: 8424-8428) were electroporated with the Pax4 gene under the control of the CMV promoter and the neomycin resistance gene under the control of the phosphoglycerate kinase I promoter (pGK-1).

ES cells were cultured in Dulbecco's modified Eagle's medium containing 4.5 g/l glucose, $10^4$ M beta-mercaptoethanol, 2 nM glutamine, 1% non-essential amino acids, 1 nM Na-pyruvate, 20% fetal calf serum (FCS) and 500 U/ml leukaemia inhibitory factor (LIF). Briefly, approximately $10^7$ ES cells resuspended in 0.8 ml phosphate buffered saline (PBS) were subjected to electroporation with 25 µg/ml of linearized expression vector (Joyner, Gene Targeting: A Practical Approach, Oxford University Press, New York, 1993). Five minutes after electroporation, ES cells were plated on petri dishes containing fibroblastic feeder cells previously inactivated by treatment with 100 µg/ml mitomycin C. One day after electroporation, culture medium was changed to medium containing 450 µg/ml G418. Resistant clones were separately isolated and cultured 14 days after applying the selection medium. Cells were always cultured at 37° C., 5% $CO_2$. These untreated and undifferentiated ES cells were used as control the experiment.

EXAMPLE 6

Differentiation of ES Cells into Insulin-Producing Cells (Referred to as 'Control, Supernatant 293 Cells' in FIG. 3)

The ES cell line R1 (wild type, 'R1' in FIG. 3) and ES cells constitutively expressing Pax4 ('Pax4' in FIG. 3) were cultivated as embryoid bodies (EB) by the hanging drop method, as described in patent application PCT/EP02/04362, published as WO 02/086107, which is incorporated herein by reference, with media as described below and in Table 1. The embryoid bodies were allowed to form in hanging drop cultures for 2 days and then transferred for three days to suspension cultures in petri dishes. At day 5, EBs were plated separately onto gelatin-coated 6 cm cell culture dishes containing a differentiation medium prepared with a base of Iscove modified Dulbecco's medium. After dissociation and replating at day 14 cells were cultured up to 40 days in the differentiation medium prepared with a base of Dulbecco's modified Eagle's medium: Nutrient Mixture F-12 (DMEM/F12) with the addition of supernatant of 293 cells without DG001.

EXAMPLE 7

Expression of Pancreas Specific Genes after Differentiation Of ES Cells into Insulin-Producing Cells Expression levels of pancreas specific genes was measured by Taqman analysis as described in Example 3. Total RNA was isolated from undifferentiated R1 and Pax4+ ES cells (control ES cells) at day 0 and differentiated R1 ES and Pax4+ ES cells at day 40. RNA preparation was done as described in Example 3 without using Trizol reagent.

Results show that markers for beta-cell differentiation function were expressed at higher levels in Pax4+ differentiated ES cells than in differentiated wild type ES cells demonstrating that activation of a pancreatic developmental control gene renders differentiation more efficient than for wild type ES cells (FIG. 3). Expression of substantial amounts of insulin in differentiated stem cells indicates that differentiated cells show a phenotype similar to beta-cells.

EXAMPLE 8

Induction of Differentiation of Insulin-Producing Cells by DG001 (Referred to as 'DG001-Enriched Supernatant' in FIG. 3)

In order to study the effect of DG001 to induce beta-cell differentiation in vitro, stable mouse embryonic stem (ES) cells expressing the Pax4 under the control of the cytomegalovirus (CMV) early promoter/enhancer region were generated as described in Example 5. Pax4 and wild type ES cells were then cultured in hanging drops or spinner cultures to allow the formation of embryoid bodies. Embryoid bodies were subsequently plated, enzymatically dissociated, and replated. After dissociation, cells were cultured in a differentiation medium containing various growth factors (see Table 1 for more detail). Additionally DG001 enriched supernatant of 293 cells was added every second day until day 40. Under such conditions, the expression of insulin was induced by DG001 (FIG. 3). By comparison, wild type ES cells did contain only very small numbers of insulin-producing cells at the same stage. These data demonstrate that DG001 can significantly promote and enhance ES cells differentiation into insulin-producing cells compared to wild type ES cells.

The results shown in FIG. 3 clearly demonstrate a significant induction of the differentiation of insulin-producing cells, if DG001 is added on later stages of differentiation. Thus, DG001 has a strong inductive effect on the differentiation of insulin-producing beta cells.

TABLE 1

Protocol for the induction of differentiation of insulin-producing cells by DG001

| Day | Stage of Cultivation | Medium | Coating and Analysis |
|---|---|---|---|
| 0 | hanging drops (600 cells/drop) | Iscove + 20% FCS | RNA (ES cells) |
| 1 | | | |
| 2 | EBs in suspension | Iscove + 20% FCS | |
| 3 | | | |
| 4 | | | |
| 5 | plating of EBs | Iscove + 20% FCS | gelatin coating RNA (EBs) |
| +1 | | | ornithine/ |
| +2 | | | laminin coating |
| +3 | | | |
| +4 | | | |
| +5 | | | |
| +6 | | | |
| +7 | | | |
| +8 | | | |
| +9 | dissociation | N2 + B27 + NA + 10% FCS | RNA (1 × 6 cm dish) |
| +10 | medium change | N2 + B27 + NA + DG001 enriched supernatant | |
| +11 | | | |
| +12 | medium change | +DG001 enriched supernatant | |
| +13 | | | |
| +14 | medium change | +DG001 enriched supernatant | |
| +15 | | | |
| +16 | medium change | +DG001 enriched supernatant | |
| +17 | | | |
| +18 | medium change | +DG001 enriched supernatant | |
| +19 | | | |
| +20 | medium change | +DG001 enriched supernatant | |
| +21 | | | |
| +22 | medium change | +DG001 enriched supernatant | |
| +23 | | | |
| +24 | medium change | +DG001 enriched supernatant | |
| +25 | | | |
| +26 | medium change | +DG001 enriched supernatant | |
| +27 | | | |
| +28 | medium change | +DG001 enriched supernatant | |
| +29 | | | |
| +30 | medium change | +DG001 enriched supernatant | |
| +31 | | | |
| +32 | medium change | +DG001 enriched supernatant | RNA |

Media B2 and B27 are described in Rolletschek et al., (2001) Mech. Dev. 105: 93-104.

EXAMPLE 9

Functional Characterisation of the Differentiated Insulin-Producing Cells

One important property of beta-cells is glucose responsive insulin secretion. To test whether the Pax4 derived insulin-producing cells possessed this glucose responsive property, an in vitro glucose responsive assay can be performed on the differentiated cells. On the day of the assay, the differentiation medium of 12 or 6 well plate is removed and the cells are washed 3 times with Krebs Ringer Bicarbonate Hepes Buffer (KRBH; 125 mM NaCl, 4.74 mM KCl, 1 mM $CaCl_2$, 1.2 mM $KH_2PO_4$, 1.2 mM $MgSO_4$, mM $NaHCO_3$, 25 mM Hepes, pH 7.4 and 0.1% BSA) supplemented with 2.8 mM Glucose. For preincubation cells are incubated in KRBH+2.8 mM Glucose for 2 hours at 37° C. Afterwards cells are incubated in 500 ml KRBH+2.8 mM Glucose for 1 hour and the supernatant is then kept for measurement of basal insulin secretion. For the stimulated insulin release 500 ml KRBH containing 27.7 mM glucose are added to the cells. After 1 hour incubation at 37° C., the supernatant is recovered for measurement of glucose-induced insulin secretion and the cells were extracted with acid-ethanol (see also Irminger, J.-C. et al., 2003, Endocrinology 144: 1368-1379). Insulin levels are determined by an Enzyme-Linked Immunosorbent Assay (ELISA) for mouse insulin (Mercodia) and performed according to the manufacturer's recommendations.

EXAMPLE 10

Transplantation of Pax4 ES Derived Insulin-Producing Cells in STZ Diabetic Mice The therapeutic potential of DG001 induced insulin-producing cells to improve and cure diabetes can be investigated by transplanting the cells into streptozotocin induced diabetic mice. Streptozotocin is an antibiotic which is cytotoxic to beta-cells when administered at certain dosage (see Rodrigues et al.: Streptozotocin-induced diabetes, in McNeill. (ed) Experimental Models of Diabetes, CRC Press LLC, 1999). Its effect is rapid, rendering an animal severely diabetic within 48 hours.

Non-fasted Male BalbC mice can be treated with STZ to develop hyperglycaemia after STZ treatment. Mice are considered diabetic if they have a blood glucose level above 10 mmol/l for more than 3 consecutive days. Cells are transplanted under the kidney capsule and into the spleen of animals. The presence of the insulin-producing cells can be confirmed by immunohistological analysis of the transplanted tissue. Results are expected to demonstrate that the transplanted cells can normalise blood glucose in diabetic animals.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method for differentiating stem cells into insulin-producing cells comprising culturing said stem cells in a culture medium comprising human pleiotrophin (SEQ ID NO: 2) or a fragment thereof in an amount effective to produce insulin-producing cells.

2. The method according to claim 1, wherein the stem cells have been modified to constitutively express the PAX-4 gene.

3. The method according to claim 1, wherein the stem cells are embryonic stem cells, adult stem cells, somatic stem cells or primordial germ cells.

4. The method according to claim 1, wherein the stem cells are of human origin.

5. The method according to claim 1, wherein the stem cells are cultured with human pleiotrophin comprising SEQ ID NO: 2.

6. The method according to claim 1, wherein the stem cells are aggregated to form embryoid bodies.

* * * * *

UNITED STATES PATENT AND TRADEMARK OFFICE
CERTIFICATE OF CORRECTION

PATENT NO. : 8,501,473 B2
APPLICATION NO. : 10/564769
DATED : August 6, 2013
INVENTOR(S) : Onichtchouk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1933 days.

Signed and Sealed this
Fifteenth Day of September, 2015

Michelle K. Lee
*Director of the United States Patent and Trademark Office*